United States Patent
Lee et al.

(10) Patent No.: US 7,229,539 B1
(45) Date of Patent: Jun. 12, 2007

(54) DESTRUCTIBLE SURFACTANTS AND USES THEREOF

(75) Inventors: Peter Jeng Jong Lee, Westborough, MA (US); Bruce J. Compton, Lexington, MA (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 10/169,002

(22) PCT Filed: May 12, 2000

(86) PCT No.: PCT/US00/13028

§ 371 (c)(1),
(2), (4) Date: Sep. 18, 2002

(87) PCT Pub. No.: WO00/70334

PCT Pub. Date: Nov. 23, 2000

Related U.S. Application Data

(60) Provisional application No. 60/134,113, filed on May 14, 1999.

(51) Int. Cl.
*G01N 27/447* (2006.01)
*G01N 27/453* (2006.01)
*G01N 30/02* (2006.01)
*B01D 15/08* (2006.01)
*C11D 3/00* (2006.01)

(52) U.S. Cl. ............. 204/450; 204/451; 204/456; 204/466; 210/656; 422/70; 436/161; 510/357; 510/426

(58) Field of Classification Search ........ 204/450–469, 204/601–621; 422/70; 210/656; 436/516, 436/161, 162; 250/282; 510/357, 426
See application file for complete search history.

(56) References Cited

U.S. PATENT DOCUMENTS

| 3,948,953 | A | | 4/1976 | McCoy |
| 4,925,567 | A | * | 5/1990 | McAleese ................ 210/656 |
| 5,523,566 | A | * | 6/1996 | Fuerstenau et al. ......... 250/282 |
| 5,607,910 | A | * | 3/1997 | Sherry et al. .............. 510/235 |
| 5,817,930 | A | * | 10/1998 | Cojean et al. ............. 73/61.52 |
| 5,961,801 | A | * | 10/1999 | Hui-Shieh et al. .......... 204/469 |
| 6,096,692 | A | | 8/2000 | Hagihara et al. |

FOREIGN PATENT DOCUMENTS

| EP | 0242148 A2 | * 10/1987 |
| PL | 177120 | 9/1999 |
| WO | WO 00/70334 | 11/2000 |
| WO | WO 03/102225 | 12/2003 |
| WO | WO 03/102536 | 12/2003 |

OTHER PUBLICATIONS

CAPLUS abstract for Polish Patent PL-175563 (Piasecki et al.) Jan. 29, 1999.*

(Continued)

*Primary Examiner*—Alex Noguerola
(74) *Attorney, Agent, or Firm*—Edwards Angell Palmer & Dodge LLP; Peter C. Lauro, Esq.

(57) ABSTRACT

Destructible surfactants and methods of using same are provided. The invention includes anionic surfactants having a dioxolane or dioxane functional group which enables the surfactant to be broken down under acidic conditions. The invention also includes methods of making anionic surfactants and methods of using anionic surfactants in a variety of applications.

20 Claims, 15 Drawing Sheets

OTHER PUBLICATIONS

Piasecki et al. ("Chemical Structure and Surface Activity XXXII. Synthesis and Surface Properties of Chemodegradable Surfactants: Sodium cis-[(2-n-alkyl-5-methyl-1,3-dioxan-5-yl)methyl] Sulfates", Bulletin of the Polish Academy of Sciences—Chemistry, vol. 45, No. 3, 1997 pp. 329-337, month unknown.*

Yamamura ("Studies on Synthesis and Properties of Surfactants with Specific Functions," Yukagaku (1994), 43(1), 2-9), month unknown.*

CAPLUS abstract for Polish Patent PL-162441 B1, Dec. 31, 1993.*

Piasecki et al. ("Synthesis, Surface Properties, and Hydrolysis of Chemodegradable Anionic Surfactants: Diasteromerically Pure cis- and trans-2,5-Disubstituted-1,3-dioxanes," Journal of Colloid and Interface Science 192, 74-82 (1997)), month unknown.*

Davidsson, P. et al. "Characterization of Proteins From Human Cerebrospinal Fluid By a Combination of Preparative Two-Dimensional Liquid-Phase Electrophoresis And Matrix - Assisted Laser Desorption/Ionization Time-of-Flight Mass Spectrometry", Analytical Chemistry, vol. 71, No. 3, pp. 642-647 (1999).

Hatt, P.D. et al. "Concentration of, and SDS Removal From Proteins Isolated From Multiple Two-Dimensional Electrophoresis Gels"Eur. J. Biochem, vol. 246, pp. 336-343 (1997).

Kawasaki, H. et al. "Separation of Peptides Dissolved In A Sodium Dodecyl Sulfate Solution By Reversed-Phase Liquid Chromatography: Removal of Sodium Dodecyl Sulfate From Peptides Using an Ion-Exchange Precolumn", Analytical Biochemistry, vol. 186, pp. 264-268 (1990).

Laemmli, U.K, "Cleavage of Structural Proteins During The Assembly of the Head of Bacteriophage T4", Nature, vol. 227, pp. 680-685 (1970).

Park, Zee-Yong and Russell, David. H. "Identification of Individual Proteins In Complex Protein Mixtures By High-Resolution, High-Mass-Accuracy MALDI TOF-Mass Spectrometry Analysis of In-Solution Termal Denaturation/Enzymatic Digestion", Anal. Chem., vol. 73, No. 11, pp. 2558-2568 (2001).

Piasecki, Andrzej and Mayhew, Alexandra, "Synthesis And Surface Properties of Chemodegradable Anionic Surfactants: Diastereomeric (2-n-alkyl-1,3-dioxan-5-yl) Sulfates With Monovalent Counter-Ions", Journal of Surfactants and Detergents, vol. 3, No. 1, pp. 59-65 (2000).

Ross, Andrew R.S. et al. "Identification of Proteins From Two-Dimensional Polyacrylamide Gels Using A Novel Acid-Labile Surfactant", Proteomics, vol. 2, pp. 928-936, (2002).

U.S. Appl. No. 10/516,419, filed Nov. 29, 2004, Mallet et al.

U.S. Appl. No. 10/516,418, filed Nov. 29, 2004, Bouvier et al.

Russell, William K. et al. "Proteolysis In Mixed Organic-Aqueous Solvent System: Appilcations For Peptide mass Mapping Using Mass Spectrometry", Anal. Chem,; vol. 73, No. 11, pp. 2682-2685 (2001).

Schively, J.E. "Methods of protein Microcharacterization", Schively, Ed. Jumana Press, Clifton, NJ, pp. 41 (1996).

Grosse, P.Y., et al. "High-performance liquid chromatographic assay for methyl-B-cyclodextrin In plasma and cell lysate", Journal of Chromatography B, 694 (1997) 219-226.

* cited by examiner

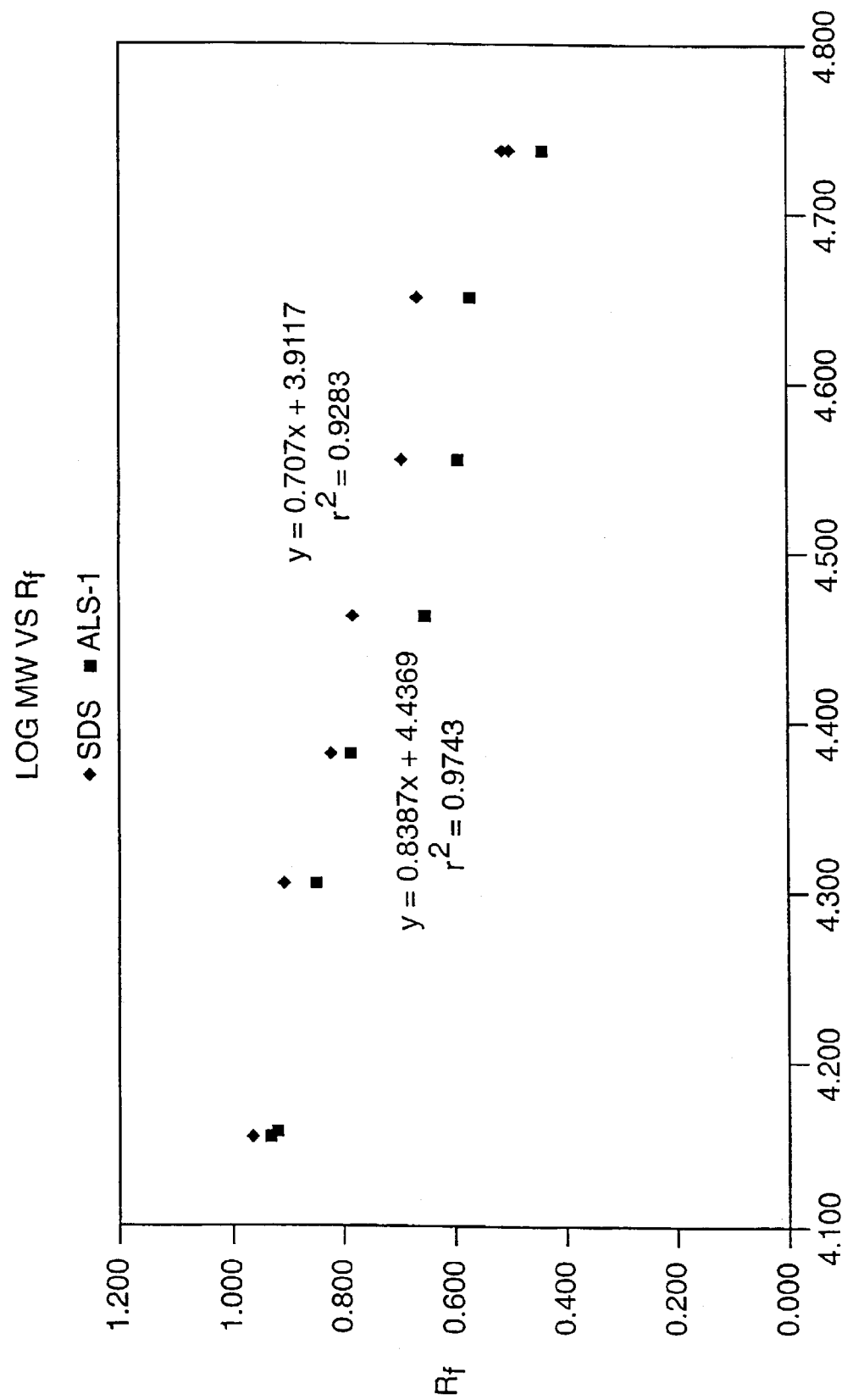

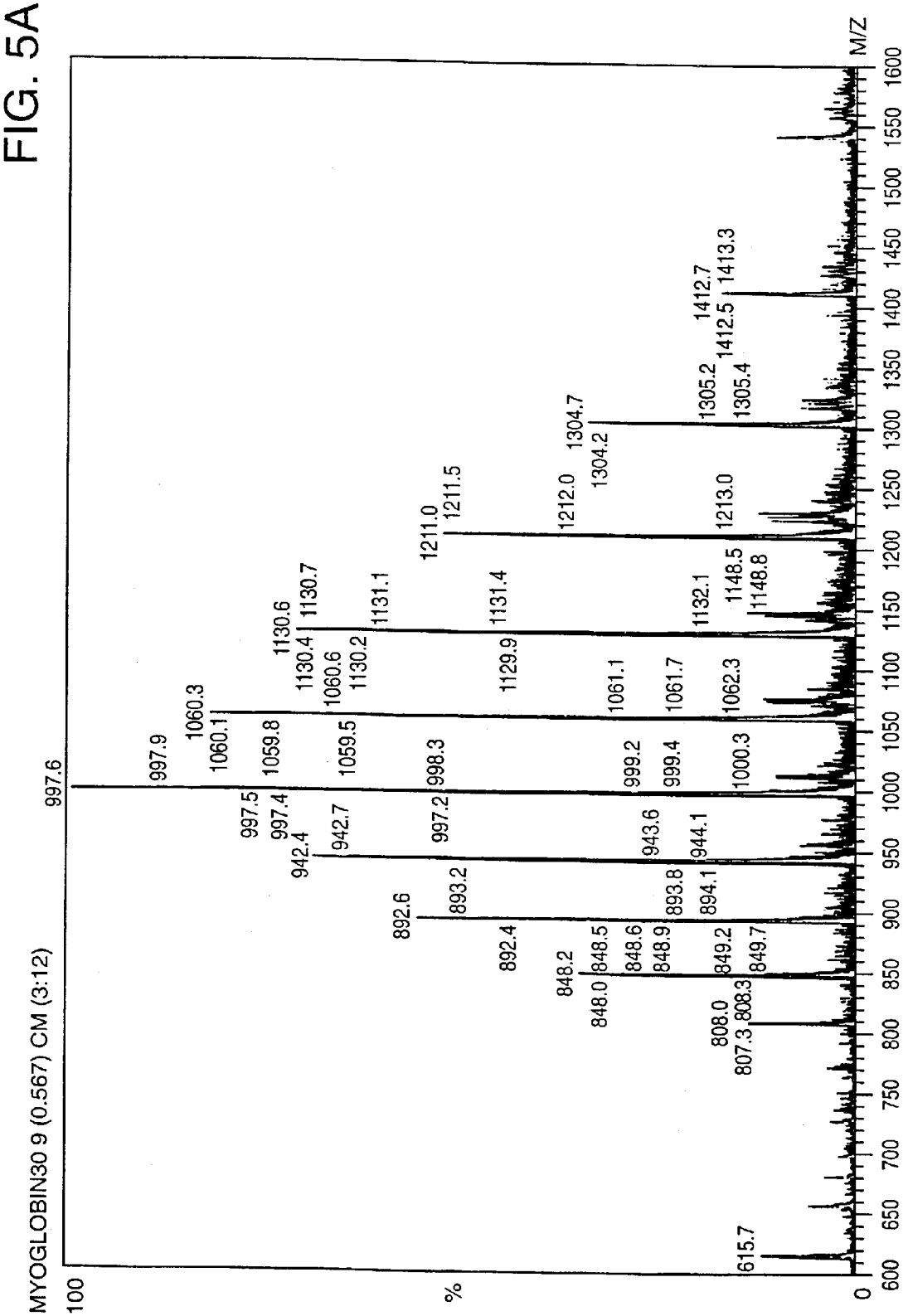

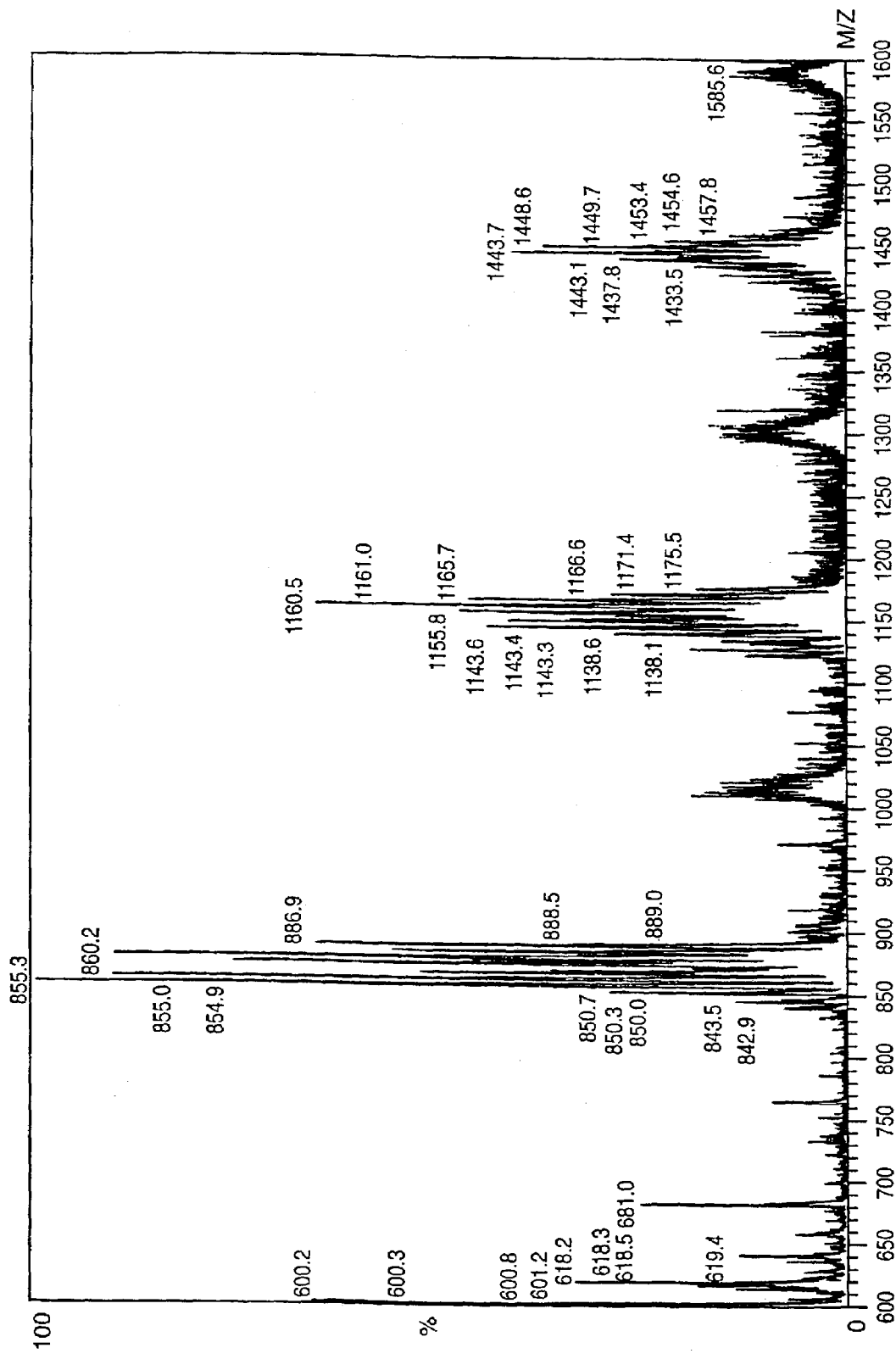

DESTRUCTIBLE SURFACTANTS AND USES THEREOF

This application claims priority under 35 U.S.C. 371 from PCT/US00/13028, filed on May 12, 2000, which claims priority from provisional application 60/134,113, filed on May 14, 1999.

FIELD OF THE INVENTION

This invention relates generally to compositions and methods for analysis and purification of large molecules, such as proteins or peptides. In particular, this invention relates to anionic surfactants which can be destroyed at relatively low pH and methods which use these surfactants. Examples of applications which will benefit from this invention include electrophoresis, ion-pair liquid chromatography, liquid chromatography, mass spectrometric detection, liquid—liquid extraction and other techniques which benefit from the initial presence and ultimate removal of a surfactant.

BACKGROUND OF THE INVENTION

Surfactants are used in a variety of applications. For example, surfactants are used commercially for cleaning manufactured items, removing paints, chemical processing, for use in emulsion polymerization, solubilizing drugs, purifying proteins, and various bioanalytical applications.

One particular bioanalytical application that uses surfactants is sodium dodecyl sulfate polyacrylamide gel electrophoresis (SDS-PAGE). In the past three decades, SDS-PAGE has been widely used as a simple and relatively rapid tool for analysis and purification of large molecules such as proteins (U. K. Laemmli, *Nature* 227, 680–685, 1970). Sodium dodecylsulfate (SDS) is an anionic surfactant that denatures proteins by forming a stable complex. Upon denaturation, SDS binds to most proteins and peptides in a constant weight ratio of about 1.4:1. As a result, the SDS-protein complexes have almost identical charge densities and therefore migrate in a polyacrylamide gel according to molecular weight. If the gel is of the correct porosity, a plot of log $M_w$ vs. relative mobility, $R_f$, results in a linear relationship. The band intensity after staining is a rough indicator of the amount present in the sample. When coupled with another electrophoretic technique, isoelectricfocusing, SDS-PAGE can separate complex mixtures into several hundred discrete components.

The ability to estimate the size and amount of a protein has led to various applications of SDS-PAGE. However, there are some drawbacks to the technology. For example, it is very difficult to use mass spectrometry to monitor and analyze samples from SDS-PAGE separations because SDS interferes with the sensitivity of mass spectrometry detection. Furthermore, it is very difficult to separate SDS from SDS/protein complex since SDS is a surfactant that forms emulsions.

Several approaches have been tried to solve these problems. Non-ionic surfactants, such as octyl β-glucopyranoside, have been used for mass spectrometric applications (P. Dainese Hatt, M. Quadroni, W. Staudenmann, and P. James, *Eur. J. Biochem.* 246, 336–343, 1997). However, the electrophoretic separation still requires SDS, and a time-consuming surfactant exchange step is needed.

Another approach is electroelution or electroblotting from the polyacrylamide gel onto a PVDF or nitrocellulose membrane. However, this approach often leads to significant loss in protein recovery.

Other approaches that have been tried are also time-consuming and may lead to significant protein loss are: protein precipitation with guanidium chloride (J. E. Schively, in *Methods of protein microcharacterization*; J. E. Schively, Ed., Humana Press, Clifton, N.J., 1986, p. 41.), ion-pair reagents (W. H. Koningsberg and L. H. Henderson. *Methods Enzymol.* 91, 254, 1983), liquid—liquid extraction (P. Davidsson, A. Westman, M. Puchades. C. L. Nilsson, and K. Blennow, *Anal. Chem.* 71, 642–647, 1999) and reversed-phase HPLC (H. Kawasaki and K. Suzuki, *Anal. Biochem.* 186, 264, 1990).

SUMMARY OF THE INVENTION

The present invention features destructible surfactants and methods for solubilizing, analyzing, separating, purifying and/or characterizing large molecules with these surfactants. In one aspect, the invention provides anionic surfactants which may be selectively broken up at relatively low pH. The resulting breakdown products of the surfactants may be removed from the sample with relative ease. The invention has applicability in a variety of techniques which benefit from the initial presence and ultimate removal of a surfactant.

The invention provides surfactants represented by the formula (Formula I):

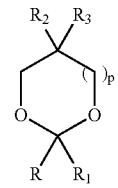

in which p is 0, 1 or 2;

R is alkyl;

$R_1$ and $R_2$ are each, independently, hydrogen or methyl; and $R_3$ is selected from $-OSO_3^-$, $-R_4OSO_3^-$, $-R_4OR_5SO_3^-$, and $-OR_5SO_3^-$, wherein $R_4$ and $R_5$ are each, independently, lower alkyl.

The invention also includes methods of preparing surfactants having the structure of Formula I.

In one embodiment, the invention pertains to methods for analyzing a sample which include contacting the sample with a surfactant having the structure of Formula I. In a preferred embodiment, the method includes analyzing the sample by high performance liquid chromatography. In another preferred embodiment, the method includes analyzing the sample by mass spectrometry. In yet another preferred embodiment, the method includes analyzing the sample by ion-pair liquid chromatography.

In another embodiment, the invention provides a method for performing electrophoresis which includes contacting a sample with a surfactant having the structure of Formula I. In a preferred embodiment, the electrophoresis is gel electrophoresis, more preferably polyacrylamide gel electrophoresis, including the tube, slab gel and capillary formats of polyacrylamide gel electrophoresis. In other preferred embodiments, the electrophoresis is free zone electrophoresis or capillary electrophoresis. In still other preferred embodiments, the methods include the step of degrading the surfactant after electrophoresis. In another preferred embodiment, the method includes degrading the surfactant after electrophoresis with a relatively acidic solution. In yet another preferred embodiment, the method includes the step of further purifying the sample after degrading the surfactant.

In still another embodiment, the invention provides a kit for performing electrophoresis which includes a surfactant having the structure of Formula I. In a preferred embodiment, the kit includes a component for degrading the surfactant. In another preferred embodiment, the kit includes a molecular weight standard. In still another preferred embodiment, the kit includes a staining reagent. In another embodiment, the surfactant of the invention is incorporated into a gel medium.

BRIEF DESCRIPTION OF THE DRAWINGS

FIG. 1 depicts a plot of $\log_{10}$ molecular weight (MW) versus relative migration factor (Rf) for Mark VI and Mark VII proteins using the data for SDS and ALS-I from Example 2.

FIG. 2 shows electrospray mass spectra of myoglobin under the various treatment conditions described in Example 3.

FIG. 3 shows electrospray mass spectra of myoglobin bands eluted from a polyacrylamide gel, as discussed in Example 4.

FIG. 4 shows electrospray mass spectra of myoglobin treated with a surfactant of the present invention, namely, 0.1% ALS-II, as described in Example 7.

FIG. 5 shows electrospray mass spectra of myoglobin using different concentrations of ALS-II. In each case, the ALS-II was degraded prior to mass spectroscopy. FIG. 5A shows the spectrum of 5 µM myoglobin in 50/50 20 mM ammonium acetate/water, 1% acetic acid and 0.005% ALS-II (w/v).

FIG. 6 shows electrospray mass spectra of myoglobin using different concentrations of SDS. FIG. 6C shows the spectrum of 5 µM myoglobin in 50/50 20 mM ammonium acetate/water, 1% acetic acid and 0.02% SDS (w/v).

DETAILED DESCRIPTION OF THE INVENTION

Figure 2A:
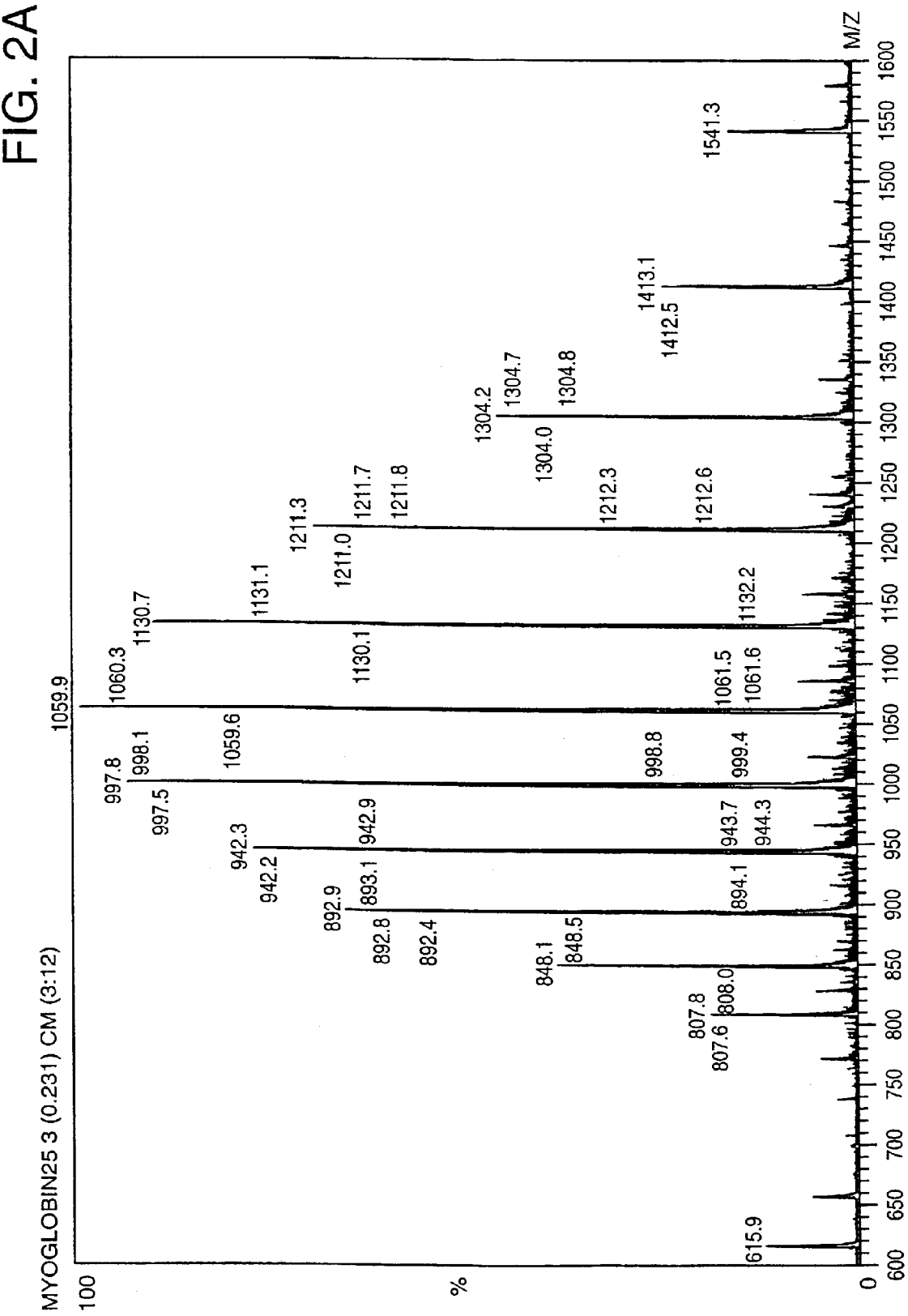
FIG. 2A is the spectrum of 5 µM myoglobin in 50/50 20 mM ammonium acetate/water with 1% acetic acid.

This invention pertains to anionic surfactants, including the synthesis and use of anionic surfactants. In particular, the invention includes anionic surfactants with protein-binding and electrophoretic properties similar to SDS. Unlike SDS, however, the surfactants of the present invention include a dioxolane or dioxane functional group which enables the surfactant to break down in an acidic environment. The resulting degradant products can be removed from the matrix more readily than the original surfactant. In addition, mass spectrometric sensitivity of proteins is significantly and surprisingly greater than in the presence of SDS at similar concentrations, even in the presence of these degradant products.

The destructible surfactants may be prepared as shown in Schemes 1–3. These surfactants have functionality similar to SDS but, unlike SDS, they may be hydrolyzed in aqueous acid solution under mild condition to give two nonsurfactant products: an ionic, water-soluble compound and a neutral, water-insoluble compound.

The surfactants of the present invention may be used in applications which benefit from the initial presence and ultimate removal of a surfactant. In particular, the present invention is useful for the solubilization, analysis, separation, purification and/or characterization of large molecules.

So that the invention may be more readily understood, a number of terms are first defined.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$–$C_{20}$ for straight chain, $C_3$–$C_{20}$ for branched chain), and more preferably 20 or fewer.

Unless the number of carbon atoms is otherwise specified, the term "lower alkyl" refers to an alkyl group having from one to ten carbons. In preferred embodiments, a lower alkyl group has 2 to 6 carbon atoms, more preferably 3 or 4 carbon atoms.

The term "sample/surfactant complex" refers to the complex formed by a surfactant of the present invention and a sample.

The term "sample" refers to any molecule that may be used in the present invention. Preferred examples include, without limitation, macromolecules, more preferably proteins or peptides.

The term "lipophilic protein" refers to proteins or peptides that are relatively hydrophobic. Preferred examples include, without limitation, protein from myelin or central nervous system tissue and membrane-bound proteins such as receptors.

The term "receptor" is recognized in the art and refers generally to membrane-bound molecules, preferably proteins, which bind a ligand and transmit a signal into the cell. Such receptors usually have an extracellular domain, a transmembrane domain, and an intracellular domain.

The term "inclusion body" is recognized in the art and refers to an intracellular structure, preferably one containing an expressed protein.

The term "solution for degrading the surfactant" refers broadly to any relatively low pH solution. Preferably, the pH of the solution is between 0 and 5, more preferably between 1 and 3. In general, the lower the pH of the solution for degrading the surfactant, the less time required to degrade the surfactant. In addition, the compound used to make the solution for degrading the surfactant is not particularly limited: any compound that provides a relatively low pH solution suitable for degrading the surfactants of the present invention without damaging the sample is sufficient. Thus, for example, hydrochloric acid may be used as the solution for degrading the surfactant. Preferably, trifluoroacetic acid (TFA) may be used, and most preferably, acetic or formic acid may be used as the solution for degrading the surfactant.

The term "electrophoresis" refers to any of the various methods of analyzing molecules by their rate of movement in an electric field, i.e. based on the charge to mass ratio of the molecules. Examples include, but are not limited to, gel electrophoresis, polyacrylamide gel electrophoresis, including the tube, slab gel and capillary formats of polyacrylamide gel electrophoresis, free zone electrophoresis and capillary electrophoresis.

The term "analysis" or "analyzing" refers to any of the various methods of separating, purifying, solubilizing, and/or characterizing large molecules, such as proteins or peptides. Examples include, but are not limited to, electrophoresis, mass spectrometry, high performance liquid chromatography, ion-pair liquid chromatography, liquid—liquid extraction and ultraviolet detection.

The term "mass spectrometric detection" refers to any of the various methods of mass spectroscopy. Examples include, but are not limited to, electrospray ionization ("ESI") and Matrix Assisted Laser Desorption Ionization ("MALDI").

In one aspect, the invention provides anionic surfactants having the structure of general formula (Formula I):

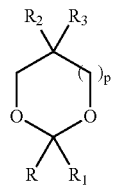

in which
p is 0, 1 or 2;
R is alkyl;
$R_1$ and $R_2$ are each, independently, hydrogen or methyl; and
$R_3$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl.

In particular, the invention provides surfactants having the structure of Formula I, with the provisos that when p is 0 and $R_1$ is methyl, $R_3$ is not $-CH_2O(CH_2)_4SO_3^-$ or, when p is 1 and $R_1$ is hydrogen and $R_2$ is methyl, $R_3$ is not $-CH_2OSO_3^-$.

In preferred embodiments, p is 0 or 1. In other preferred embodiments, R is an alkyl having from six to twenty carbon atoms, more preferably from eight to eighteen carbon atoms, and most preferably from ten to sixteen carbon atoms. Preferably, $R_3$ is $-R_4OSO_3^-$, $-R_4OR_5SO_3^-$, or $-OR_5SO_3^-$, and most preferably R3 is $-CH_2O(CH_2)_3$ $SO_3^-$ or $-CH_2O(CH_2)_4SO_3^-$. Preferably, $R_4$ and $R_5$ are each, independently, an alkyl group having from one to eight carbons, more preferably from two to six carbon atoms, and most preferably, three or four carbon atoms.

In one preferred embodiment, the invention provides anionic surfactants having the structure of general formula (Formula II):

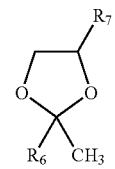

in which
$R_6$ is alkyl;
$R_7$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl.

In particular, the invention provides surfactants having the structure of Formula II, ith the proviso that when $R_6$ is $-C_9H_{19}$, $-C_{11}H_{23}$, or $-C_{13}H_{27}$, $R_7$ is not $-CH_2O(CH_2)_4SO_3^-$.

In still other embodiments, a surfactant of the invention is incorporated into a gel medium. Such gels are useful in performing electrophoresis. In one embodiment, the gel incorporated with surfactant is a polyacrylamide gel. In another aspect, the invention provides a method of synthesizing anionic surfactants having the structure of general formula (Formula I):

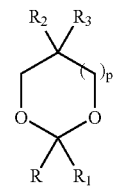

in which
p is 0, 1 or 2;
R is alkyl;
$R_1$ and $R_2$ are each, independently, hydrogen or methyl; and
$R_3$ is selected from $-OSO_3^-$, $-R_4OSO_3^-$, $-R_4OR_5SO_3^-$, and $-OR_5SO_3^-$, wherein $R_4$ and $R_5$ are each, independently, lower alkyl, the method comprising the step of reacting a compound represented by the formula:

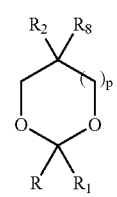

wherein R, $R_1$ and $R_2$ are defined as above and $R_8$ is hydroxyl or —$CH_2OH$, with a compound represented selected from sulfites,

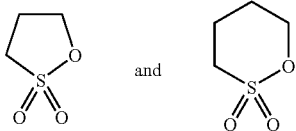

In particular, the invention provides methods of preparing surfactants having the structure of Formula I, with the provisos that when p is 0 and $R_1$ is methyl, $R_3$ is not —$CH_2O(CH_2)_4SO_3^-$ or, when p is 1 and $R_1$ is hydrogen and $R_2$ is methyl, $R_3$ is not —$CH_2OSO_3^-$.

In preferred embodiments, p is 0 or 1. In other preferred embodiments, R is an alkyl having from six to twenty carbon atoms, more preferably from eight to eighteen carbon atoms, and most preferably from ten to sixteen carbon atoms. Preferably, $R_3$ is —$R_4OSO_3^-$, —$R_4OR_5SO_3^-$, or —$OR_5SO_3^-$, and most preferably R3 is —$CH_2O(CH_2)_3SO_3^-$ or —$CH_2O(CH_2)_4SO_3^-$. Preferably, $R_4$ and $R_5$ are each, independently, an alkyl group having from one to eight carbons, more preferably from two to six carbon atoms, and most preferably, three or four carbon atoms.

As indicated in more detail in the Examples, the methods of synthesis of the present invention produce isomers. Although the methods of using surfactants of the invention do not require separation of these isomers, such separation may be accomplished, if desired, by methods known in the art. For example, preparative high performance liquid chromatography methods may be used for isomer purification.

In yet another aspect, the invention provides methods for analyzing a sample by contacting a sample with a surfactant represented by the general formula (Formula I):

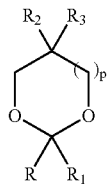

in which
p is 0, 1 or 2;
R is alkyl;
$R_1$ and $R_2$ are each, independently, hydrogen or methyl; and
$R_3$ is selected from —$OSO_3^-$, —$R_4OSO_3^-$, —$R_4OR_5SO_3^-$, and —$OR_5SO_3^-$,
wherein $R_4$ and $R_5$ are each, independently, lower alkyl; and analyzing the sample.

In preferred methods of analysis, p is 0 or 1. In other preferred embodiments, R is an alkyl having from six to twenty carbon atoms, more preferably from eight to eighteen carbon atoms, and most preferably from ten to sixteen carbon atoms. Preferably, $R_3$ is —$R_4OSO_3^-$, —$R_4OR_5SO_3^-$, or —$OR_5SO_3^-$, and most preferably $R_3$ is —$CH_2O(CH_2)_3SO_3^-$ or —$CH_2O(CH_2)_4SO_3^-$. Preferably, $R_4$ and $R_5$ are each, independently, an alkyl group having from one to eight carbons, more preferably from two to six carbon atoms, and most preferably, three or four carbon atoms. In certain embodiments, the sample may be heated either before or after contacting the sample with a surfactant of the invention.

In one preferred embodiment, the method of analysis includes a surfactant having the structure of general formula (Formula II):

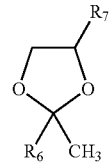

in which
$R_6$ is alkyl;
$R_7$ is selected from —$OSO_3^-$, —$R_4OSO_3^-$, —$R_4OR_5SO_3^-$, and —$OR_5SO_3^-$,
wherein $R_4$ and $R_5$ are each, independently, lower alkyl.

In other preferred embodiments, the step of analyzing the sample includes electrophoresis. In preferred embodiments, the electrophoresis is gel electrophoresis, free zone electrophoresis or capillary electrophoresis. In a particularly preferred embodiments, the electrophoresis is polyacrylamide gel electrophoresis, including the tube, slab gel and capillary formats of polyacrylamide gel electrophoresis.

In still other preferred embodiments, the step of analyzing the sample includes mass spectrometric determination, high performance liquid chromatography, ion-pair liquid chromatography, liquid—liquid extraction, or ultraviolet detection.

In one aspect, this invention uses destructible surfactants to complex with protein mixtures for polyacrylamide gel electrophoresis. After the electrophoretic separation, the proteins are freed from surfactants by treating the gel with acid solution. The protein mixtures may be further purified by conventional separation methods such as liquid—liquid extraction, solid-phase extraction or liquid chromatography. This ability to free proteins from surfactants easily after polyacrylamide gel electrophoresis may be used in various applications, with significant benefits to separation science.

As demonstrated by the PAGE results herein, proteins treated with the acid-labile surfactants of the present invention migrate in a similar pattern to proteins treated with SDS. In addition, the gel staining procedures are similar in the presence of either ALS or SDS.

Figure 2B:
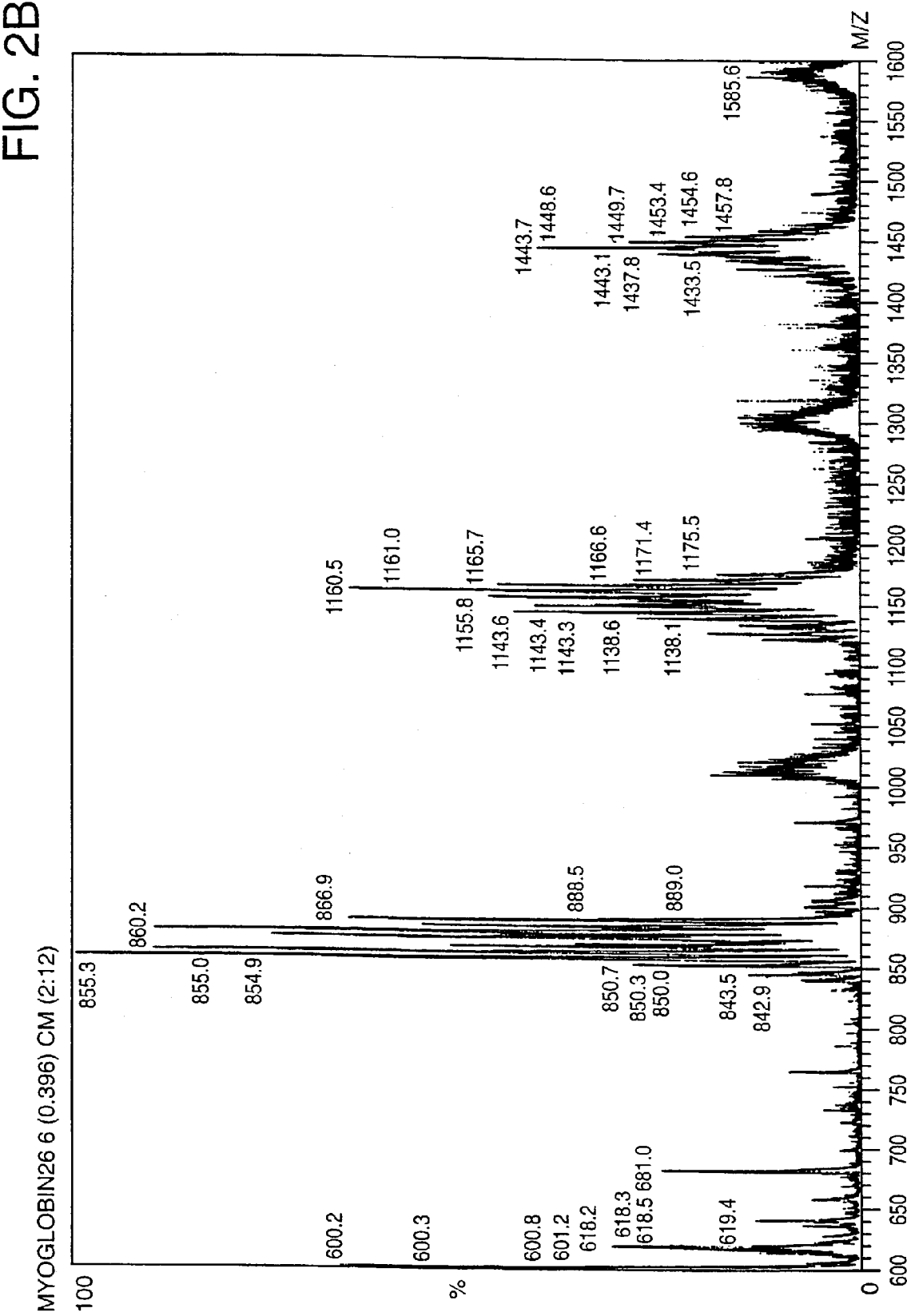
FIG. 2B is the spectrum of 5 µM myoglobin in 50/50 20 mM ammonium acetate/water with 1% acetic acid and 0.1% SDS.
Figure 2C:
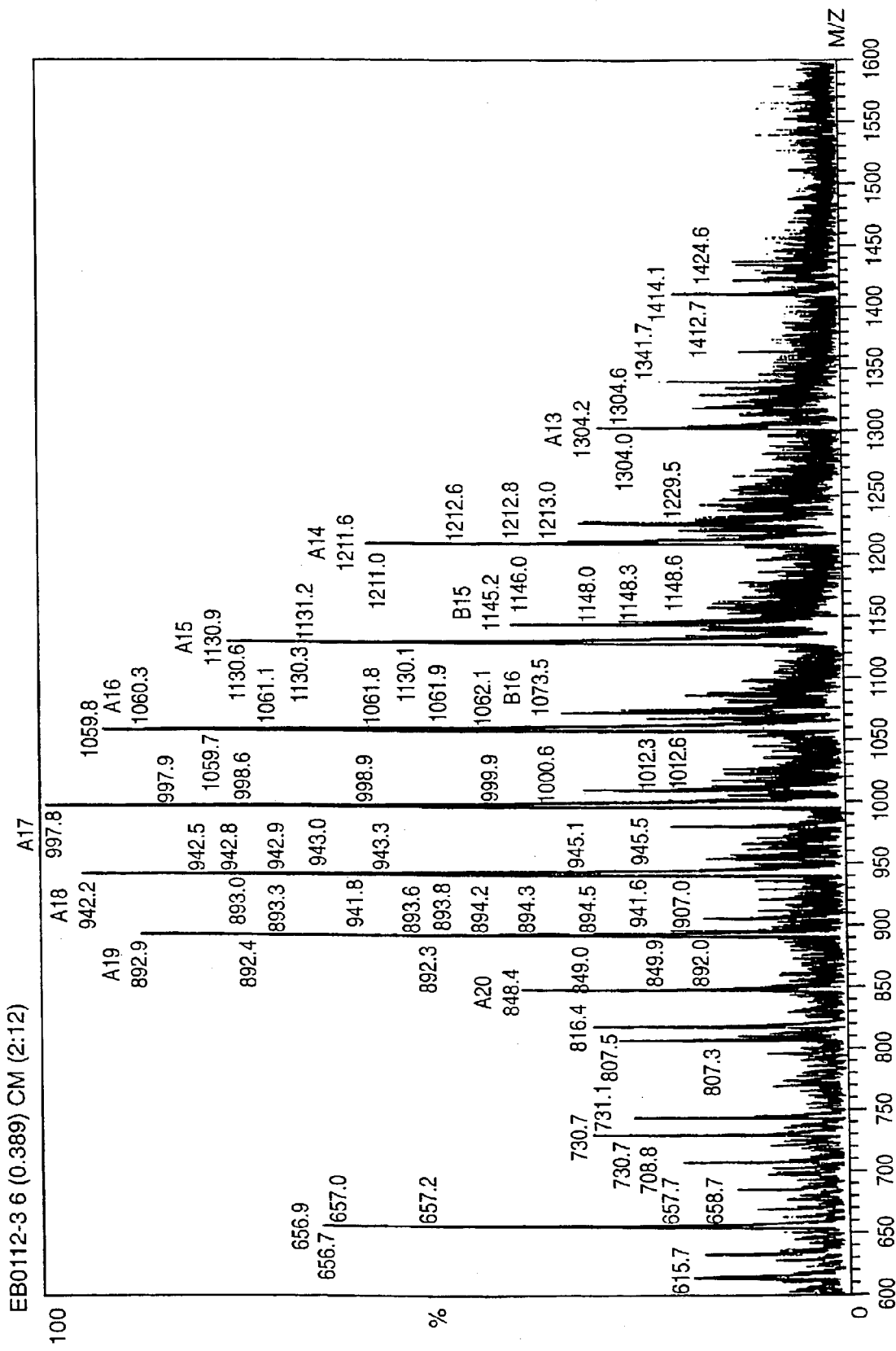
FIG. 2C is the spectrum of 5 µM myoglobin in 50/50 20 mM ammonium acetate/water with 1% acetic acid and 0.1% ALS-I that had reacted in 10% acetic acid for 16 hours.
Figure 3A:
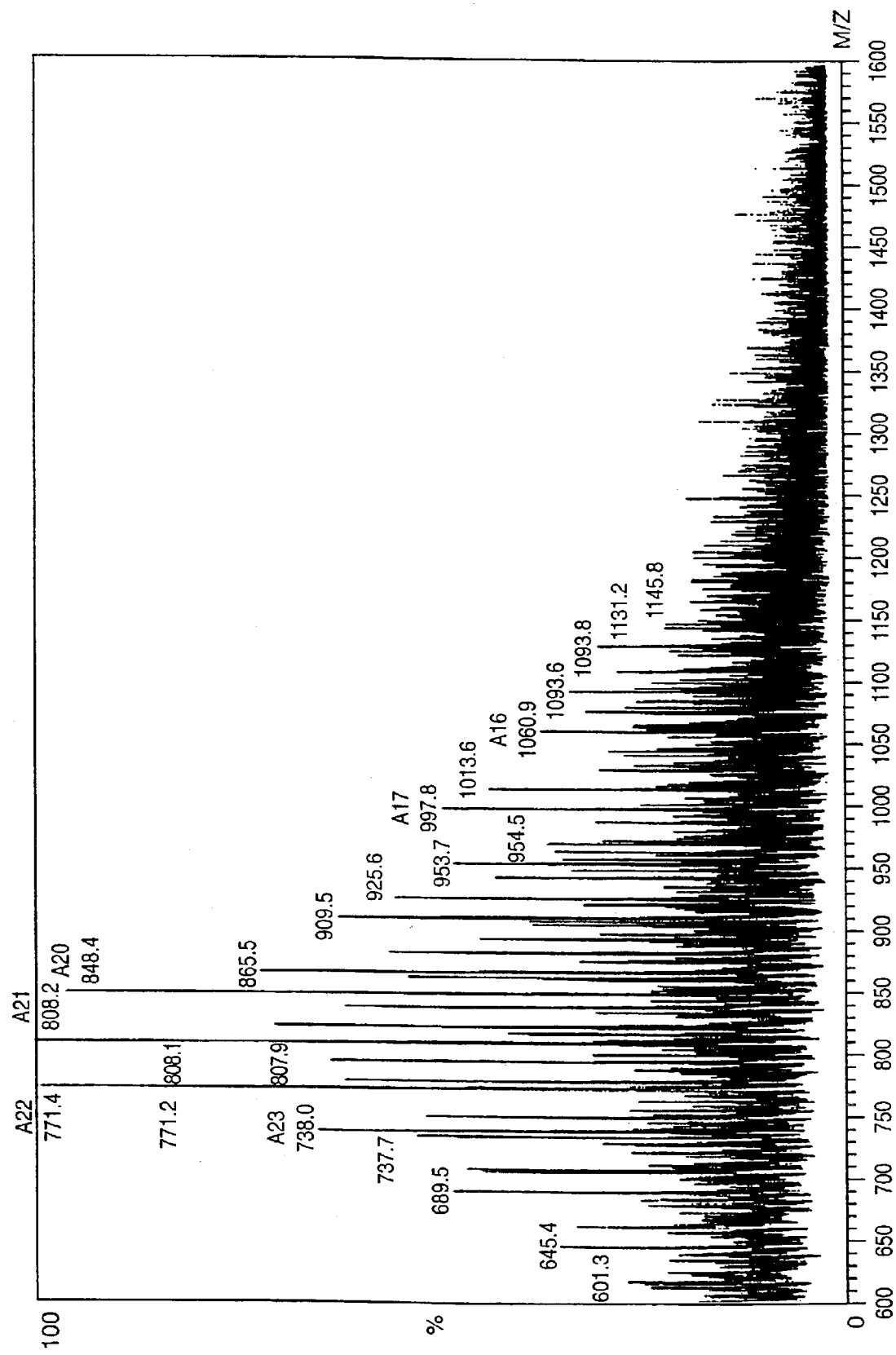
FIG. 3A is the spectrum of the myoglobin sample treated with SDS.
Figure 3B:
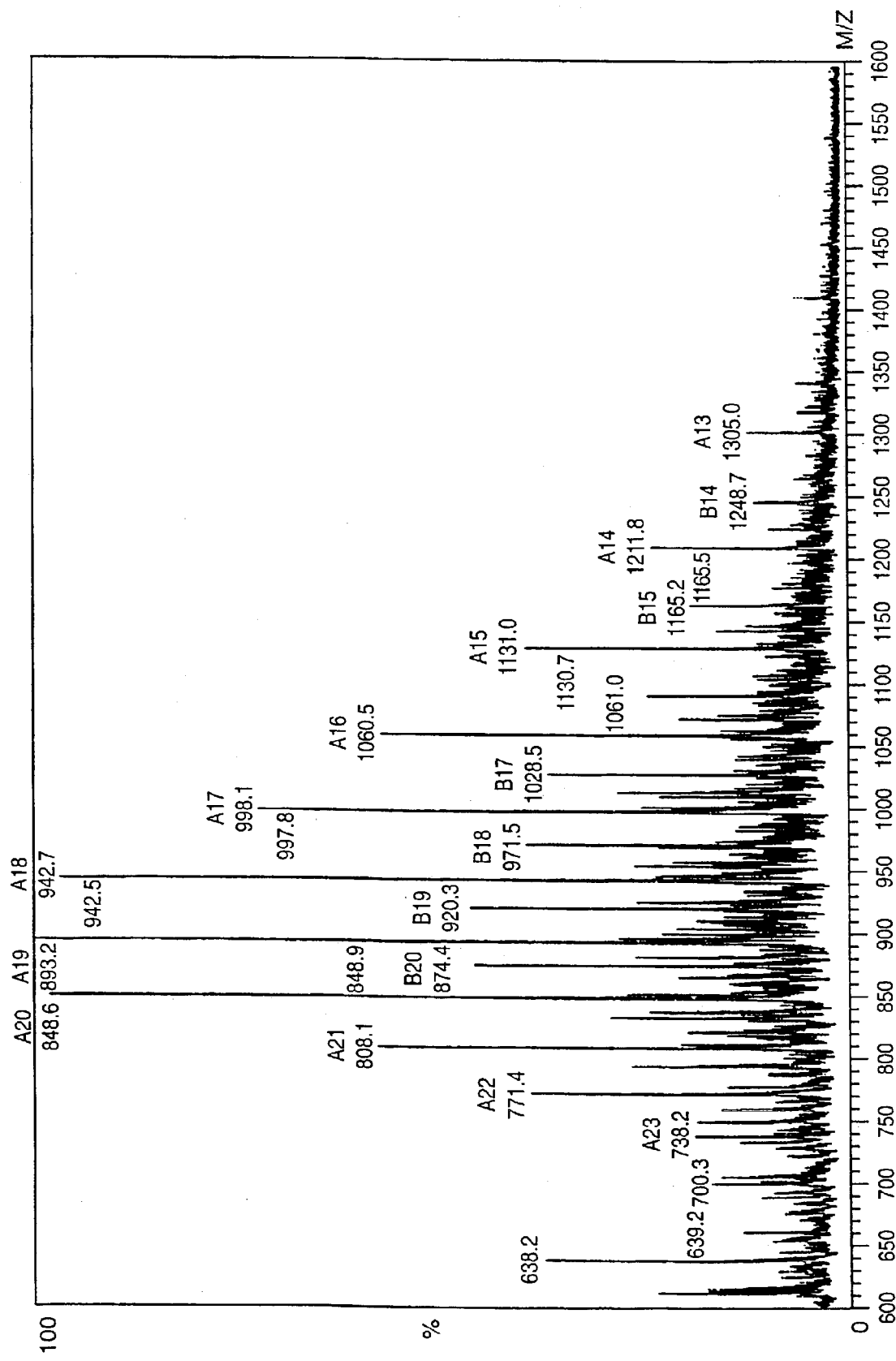
FIG. 3B is the spectrum of the myoglobin sample treated with ALS-I.

In another aspect of the invention, the sensitivity of mass spectrometric detection of proteins in the presence of degraded ALS is much greater than in the presence of SDS. The anionic surfactants of the present invention provide surprising advantages over SDS. For example, in FIGS. 2B & 3A, which is the mass spectrum of myoglobin treated with SDS, no signals due to myoglobin are observed. In contrast, as seen in FIGS. 2C & 3B, the mass spectrum of myoglobin treated with a surfactant of the present invention, after degradation, exhibits a strong myoglobin signal. Without wishing to be bound by any particular theory, this result is believed to be due to at least two effects: 1) few, if any, micelles are present with the degraded surfactant of the present invention; and 2) fewer adducts of sample and the degraded surfactant of the invention are formed. These effects allow better sensitivity in mass spectrometry than is possible when SDS is used.

The invention also provides methods for solubilizing various substances, such as inclusion bodies, lipophilic proteins, such as receptors and other membrane-bound proteins, and biological tissue. In a particularly preferred embodiment, the invention provides a method for obtaining a protein expressed in a cell by treating the inclusion bodies of the cell with a surfactant having the structure of Formula I.

In yet another embodiment, the invention provides a method for cleaning and/or regenerating HPLC columns. In a preferred embodiment, a surfactant having the structure of Formula I is contacted with the sorbent of an HPLC column such that proteins bound to the column are removed.

EXEMPLIFICATION

Example 1

Preparation of Sodium 4-[(2methyl-2 undecyl-1,3 dixolan-4-yl)methoxyl]-1-propanesulfonate(3,4) [ALS-I]

This example describes the preparation of certain anionic surfactants of the present invention. Various modifications to the following procedures will be routine to one of ordinary skill in the art, in light of the teachings herein. For example, in the following procedures, toluene may be substituted for benzene. In addition, any solvent that provides a good yield may be used in the recrystalization step.

1. Synthesis of 4 hydroxymethyl-2 methyl-2 undecyl-1,3 dixolane (1,2)

Firstly, 100 g (0.5 mol) of 2-tridecanone (Aldrich P/N 17,283-9), 56 g (0.6 mol) of glycerol (Aldrich P/N 32,00-5), 200 mL of benzene, and 1.8 grams of p-toluenesulfonic acid (Aldrich P/N 40,2885) were placed in a 500 mL round bottom flask fitted with a Dean Stark apparatus. The mixture was heated to reflux with stirring until no further separation of water appeared. The reaction mixture was cooled to room temperature and washed successively with a 100 mL portion of 5% sodium carbonate solution and three 100 mL portions of water. The organic layer was dried over sodium sulfate, filtered and the benzene was removed with a rotary evaporator. The residual oil was fractionated by distillation under reduced pressure to give the desired product (b.p. 140° C./0.3 mm Hg). The identity of the product was confirmed by $^1$H NMR in $CDCl_3$.

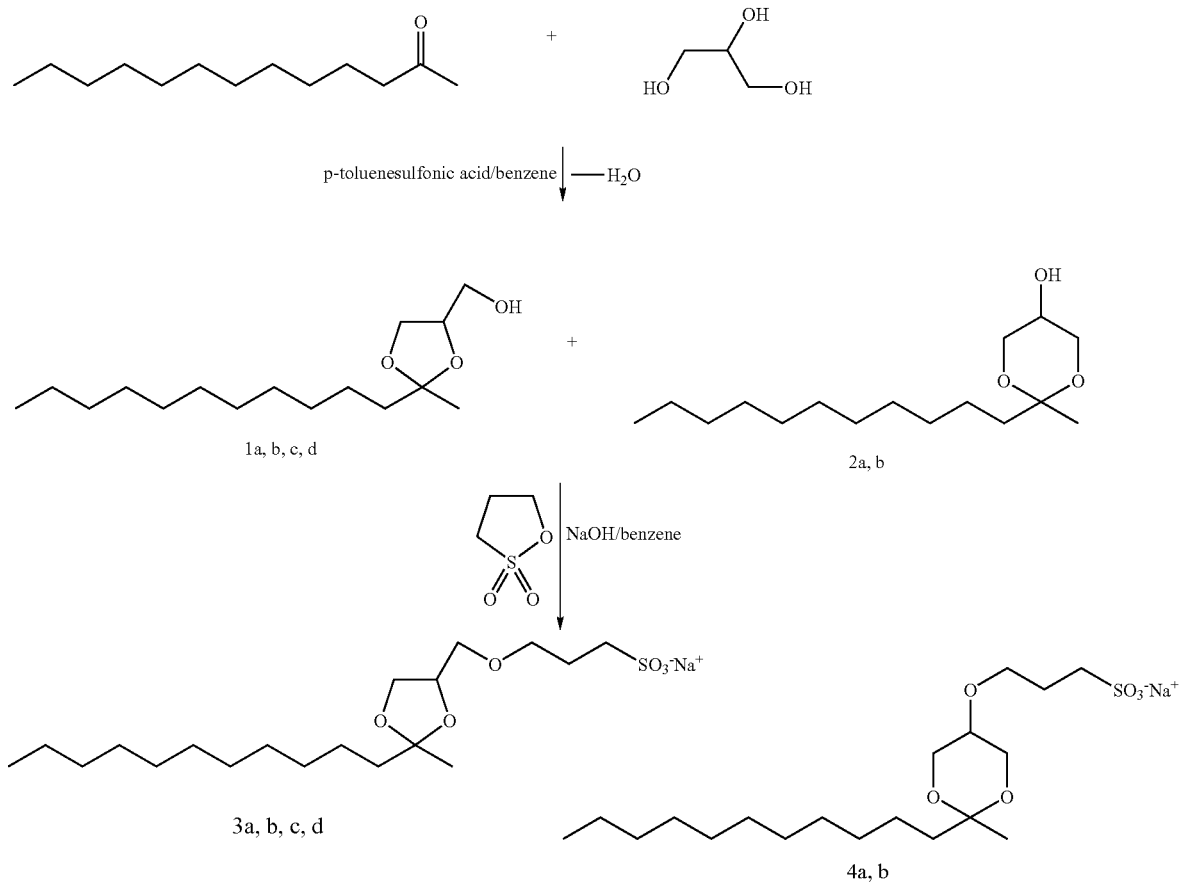

2. Synthesis of ALS-I:

50 g (0.18 mol) of 4 hydroxymethyl-2 methyl-2 undecyl-1,3 dixolane, 8 g (0.2 mol) of powdered sodium hydroxide and 200 mL of benzene were placed in a 4 neck 500 mL flask fitted with a condenser, mechanical stirrer and a thermometer. The suspension was stirred at a constant 50° C. while 25 g (0.2 mol) of 1,3 propanesultone (Aldrich P/N P5,070-6) was slowly added over 30 minutes. The suspension was then stirred at 70–75° C. for at least 6 hours. Upon completion, the reaction mixture was poured into 500 mL of boiling ethanol. The resulting mixture is then dried down on a rotary evaporator. The resulting solid is dissolved in boiling ethanol and hot filtered. The solid residue is extracted once with boiling ethanol, which is combined with the mother liquor. The solvent is removed in a rotary evaporator. The residue is then recrystallized from ethanol to yield the product. Identity of the product was confirmed by $^1$H NMR in $D_2O$.

Example 2

Polyacrylamide Gel Electrophoresis of Protein Standards Treated with ALS-I or SDS This example uses polyacrylamide gel electrophoresis to compare a surfactant of the present invention to SDS.

Polyacrylamide gel electrophoresis was performed on protein standards using either 0.1% SDS or 0.1% ALS-I. Pre-cast 12% tris-glycine gels (Novex, P/N EC6005) were inserted into a Mini-Cell II electrophoresis device (Novex, P/N EI9001). The upper and lower buffer chambers were filled with 1×Running Buffer, consisting of 0.025M Tris (Aldrich, 15456-3). 0.192 M glycine (Aldrich, G620-1), and either 0.1% SDS or 0.1% ALS-1, pH 8.3.

Molecular weight standards were prepared as follows: Mark VI protein standards (containing 13.5 mg of lysozyme, β-lactogobulin, trypsinogen, pepsin, egg albumin, bovine albumin and bromphenol tracking dye) (Sigma, P/N SDS-6) and Mark VII protein standards (containing 13.5 mg each of α-lactalbumin, trypsin inhibitor, trypsinogen, carbonic anhydrase, glyceraldehyde-3-phosphate dehydrogenase, egg albumin and bovine albumin) (Sigma. P/N SDS-7) were reconstituted in 0.6 mL of buffer containing 0.125 M Tris-Cl, (Sigma, T-3253), 20% (v/v) Glycerol (Aldrich, 32000-5), 0.02% (w/v) Bromphenol Blue (Sigma. B-6131), pH 6.8. 30 µL of each of the standards were combined with 50 µL of deionized water and 20 µL of 10% surfactant (SDS or ALS-I). A 50 µL aliquot of each sample was removed and heated to 60° C. for 10 minutes to ensure protein denaturation.

Electrophoresis was performed at a constant current of 20 mA per gel, until the bromphenol blue tracking dye was 5 mm from the end of the gel (approximately 1 hour 20 minutes).

SDS-PAGE gels were stained with zinc-imidazole Stain (Bio-Rad, 161–0440) as follows: Solution A (imidazole) and Solution B (zinc sulfate) were both diluted 1:10 with deionized water. Gels were placed in a container with dilute Solution A and mixed at low speed for 10 minutes. The gel was then transferred to Solution B, and allowed to develop 30–60 seconds. After full development, the gel was then transferred to a container with deionized water and rinsed for 3 minutes. This rinse procedure was repeated with fresh deionized water.

Gels run with ALS-I were stained using a modification of the zinc-imidazole staining technique developed by Fernandez-Patron et al. (*Electrophoresis* 19, 2398–2406, 1998). After electrophoresis, the gel was incubated for approximately 3 minutes in 200 M zinc sulfate (Sigma, Z-0501), 100 mM imidazole (Sigma, 1–0250), 0.1% ALS-I, pH 5.0. After the bands developed, the gel was rinsed in several changes of 50 mM Tris, pH 8.8 and stored.

The resulting gels revealed similar migration patterns for proteins using either SDS or ALS-I. Two proteins, carbonic anhydrase and α-lactalbumin, required heat (60° C., 10 minutes) for full denaturation using ALS-I. Plots of $\log_{10}$ MW vs. $R_f$ (protein migration distance/dye migration distance) are shown in FIG. 1. Migration of proteins on the gel using ALS-1 is similar to SDS.

Example 3

Mass Spectrometric Detection of Myoglobin Treated with ALS-I or SDS

In this example, mass spectroscopy is used to compare a surfactant of the present invention to SDS.

Mass spectrometric detection was performed on myoglobin using a Platform LC (Micromass, Manchester, UK) with constant infusion. A stock solution of 50 µM horse skeletal muscle myoglobin (Sigma. P/N M0630) was prepared in 50/50 20 mM ammonium acetate, pH 5.1/acetonitrile (v/v). A stock solution of 1% SDS and 1% ALS-I were also prepared in both 50/50 ammonium acetate/acetonitrile, and 40/40/10 ammonium acetate/acetonitrile/glacial acetic acid. The surfactant stock solutions were both prepared fresh, and allowed to sit for at least 16 hours. To 100 µL of each of the surfactant stock solutions was added 100 µL of myoglobin stock and 800 µL 50/50 ammonium acetate/acetonitrile. Each solution was then drawn into a 1 mL syringe and placed in a syringe pump (Harvard Instruments). The solution was infused into the mass spectrometer at a flow rate of 20 µL/min. Mass spectrometer settings were as follows: Gas flow rate: 340 L/h; Source temperature: 100° C., Capillary voltage: 3.46 kV; Cone voltage: 25 V; Ion energy: 0.6; Scan rate: 3.0 sec/scan; Scan range: 250–1600 amu.

Mass spectra are shown in FIG. 2. For the case where SDS is the surfactant, no signals are observed which are due to myoglobin. The spectrum of the sample containing degraded ALS-I, on the other hand, exhibits a strong myoglobin signal.

Example 4

Mass Spectrometric Detection Of Myoglobin Treated with ALS-I or SDS, Electrophoresis and Subsequent Elution from the Polyacrylamide Gel Matrix This example illustrates the use of a surfactant of the present invention in gel electrophoresis and subsequent mass spectroscopic analysis. This example also compares a surfactant of the present invention to SDS.

Polyacrylamide gel electrophoresis was performed as described in Example 2, except that myoglobin was prepared as a sample. No protein standards were used. 125 µL of a 50 µM solution of myoglobin in 0.1% TFA was diluted with 125 µL deionized water, 100 µL of 10% Surfactant and 150 µL of buffer containing 0.125 M Tris-Cl, 20% Glycerol (v/v), and 0.02% bromophenol blue, pH 6.8.

After electrophoresis, the gels were stained as described in Example 2.

Myoglobin bands were carefully excised from the gels using a clean razor. The excised gel slice was transferred to a clean tube and washed using gentle mixing in a 1 mL aliquot of 2.5 mM Tris, 19.2 mM glycine. The tris-glycine wash was repeated once. The gel slice was then washed twice in 1 mL deionized water. After the second water wash, the gel slice was removed from the tube and carefully diced to approximately 1 mm³ with a clean razor. The diced gel slice was then transferred to a clean microcentrifuge tube. 40 µL of elution solvent containing 80% Acetonitrile, 0.1% TFA was added to the tube. In this case, the trifluoroacetic acid served to degrade the surfactant. The tube was vortexed briefly and then allowed to mix overnight on a platform rocker. After the mixing period, the tubes were spun at 12,000 g to pellet the polyacrylamide gel pieces. The eluate was extracted using a gel loading pipette tip.

The eluate was analyzed by electrospray mass spectrometry. The solution was infused into the mass spectrometer at 5 µL/min. Mass spectrometer settings were as follows: gas flow rate: 276 L/hr; Capillary voltage: 3.26 kV; Cone voltage: 29 V; Ion energy; 0.6; Scan rate: 3.0 sec/scan; Scan range: 600–1600 amu. Mass spectra are shown in FIG. 3. As shown in FIG. 3A, the spectrum of the sample prepared using SDS contains a weak myoglobin signal which is obscured by adducts and other artifacts. In contrast, FIG. 3B shows that the spectrum of the sample prepared using ALS-1 displays a strong myoglobin signal.

Example 5

Preparation of Sodium 4-[(2methyl-2 undecyl-1, 3dixolan-4-yl)methoxyl]-1-butanesulfonate(5,6) [ALS-II]

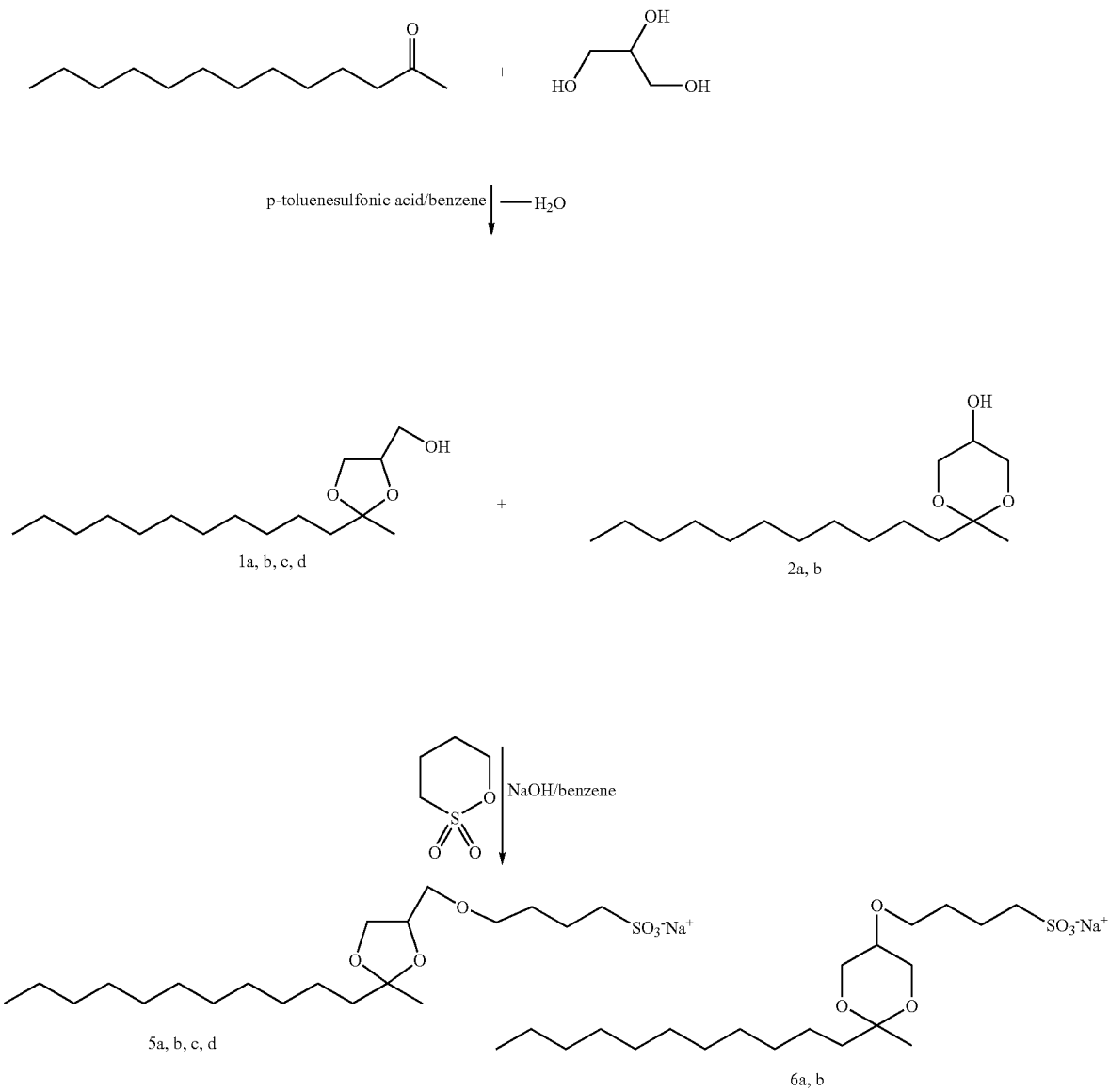

This example describes the preparation of certain anionic surfactants of the present invention. Various modifications to the following procedures will be routine to one of ordinary skill in the art, in light of the teachings herein. For example, in the following procedures, toluene may be substituted for benzene. In addition, any solvent that provides a good yield may be used in the recrystalization step.

100 g. (0.37 mol) of: 4 hydroxymethyl-2 methyl-2 undecyl-1.3 dixolane, 16.2 g (0.4 mol) of powdered sodium hydroxide and 200 mL of benzene were placed in a 4 neck 500 mL flask fitted with a condenser, mechanical stirrer and a thermometer. The suspension was stirred at a constant 50° C. while 54 g (0.4 mol) of 1,4 butanesultone (Aldrich P/N B8,550-1) was slowly added over 30 minutes. The suspension was then stirred at 70–75° C. for at least 6 hours. Upon completion, the reaction mixture was poured into 500 mL of boiling ethanol. The resulting mixture is then dried down on a rotary evaporator. The resulting solid is dissolved in boiling ethanol and hot filtered. The solid residue is extracted once with boiling ethanol, which is combined with the mother liquor. The solvent is removed in a rotary evaporator. The residue is then recrystallized from ethanol to yield the product. Identity of the product was confirmed by $^1$H NMR in $D_2O$.

Example 6

Polyacrylamide Gel Electrophoresis of Protein Standards Treated with ALS-II or SDS This example uses polyacrylamide gel electrophoresis to compare a surfactant of the present invention to SDS.

Electrophoresis of protein standards with either ALS-II or SDS and subsequent staining was performed using the same procedure described in Example 2

Example 7

Mass Spectrometric Detection of Myoglobin Treated with ALS-II or SDS

In this example, mass spectroscopy is used to compare a surfactant of the present invention to SDS. In addition, the effect of surfactant concentration is examined.

Figure 4A:
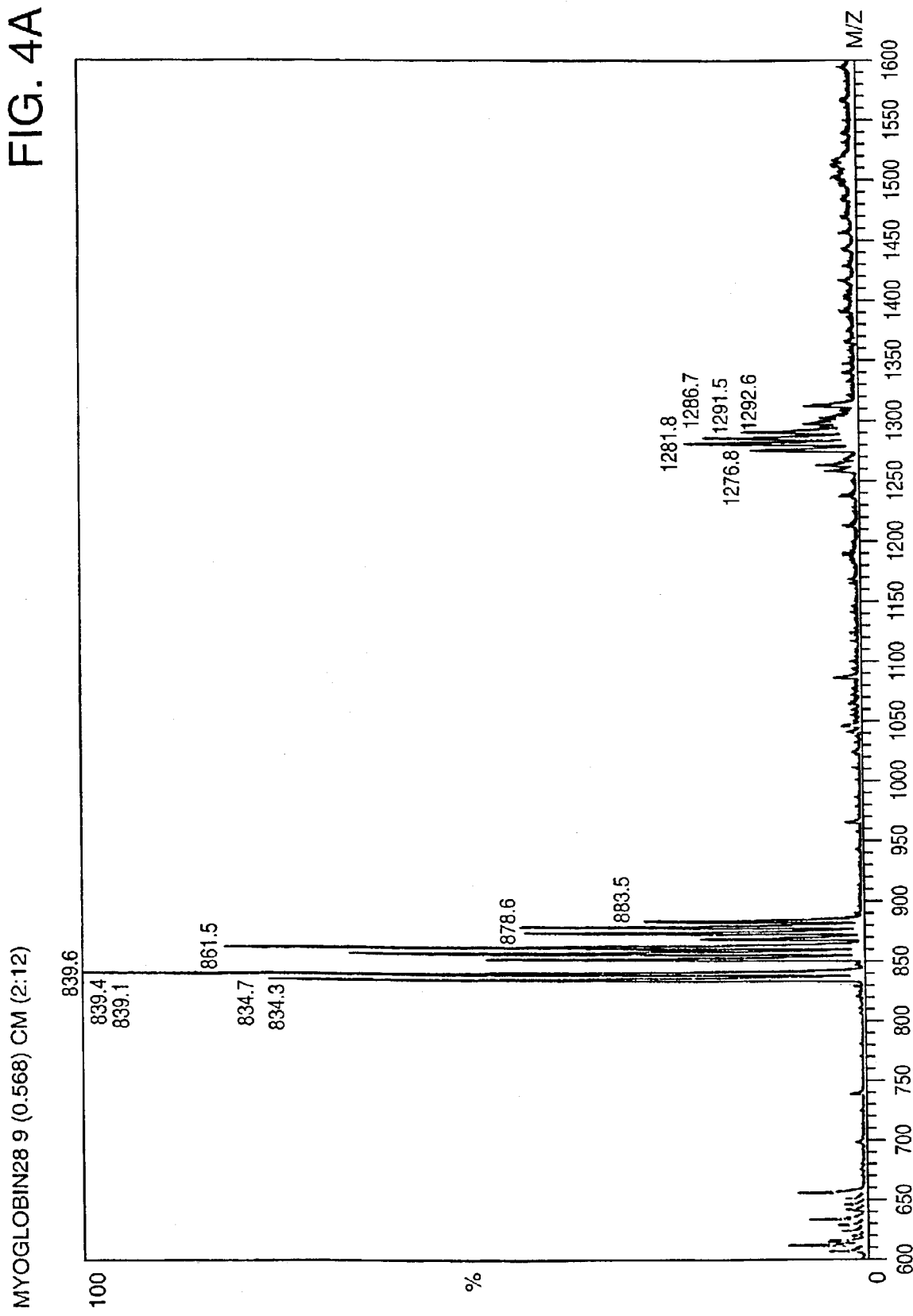
FIG. 4A shows the spectrum of 5 µM myoglobin in 50/50 20 mM ammonium acetate/water, 1% acetic acid with freshly prepared 0.1% ALS-II.
Figure 4B:
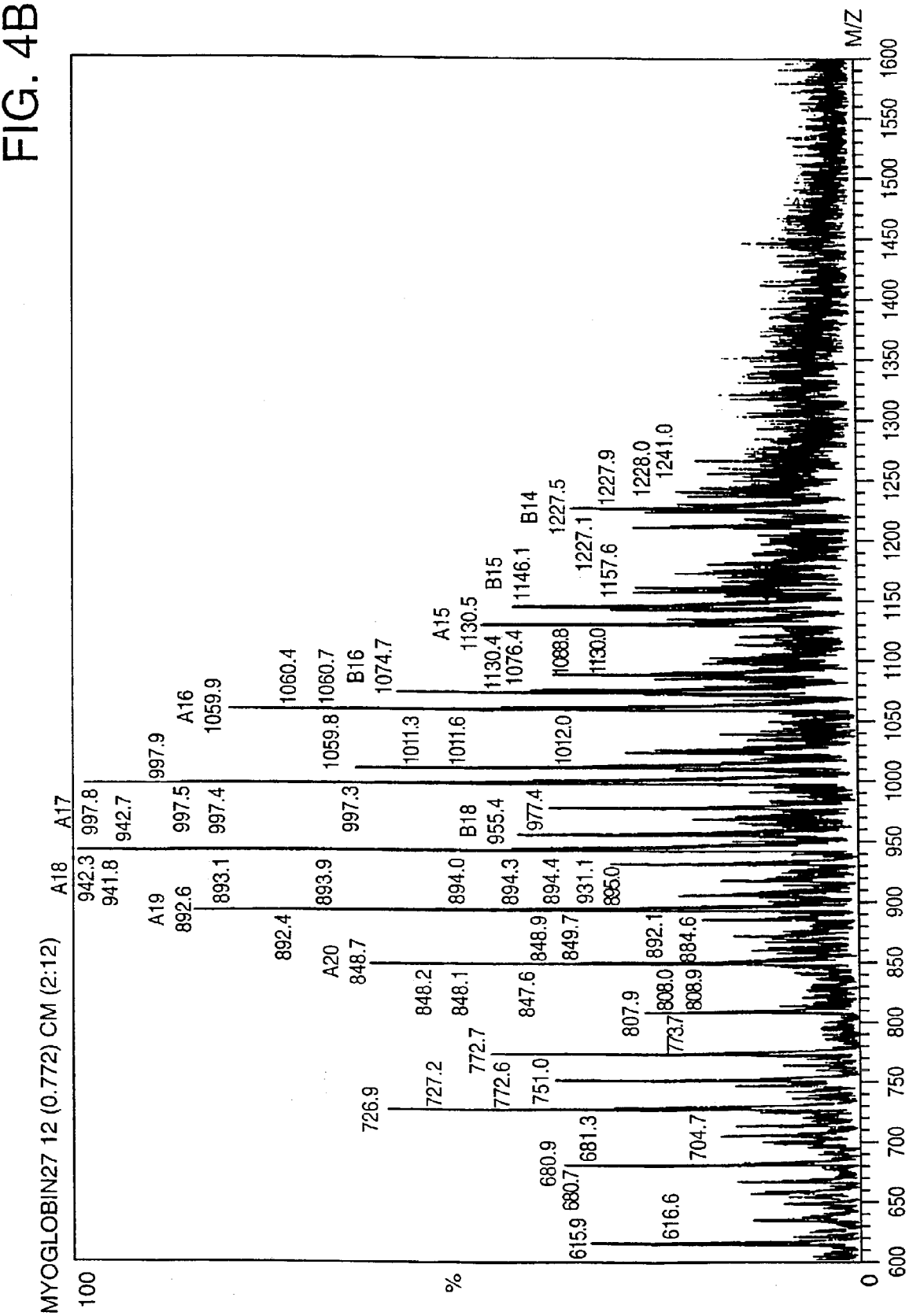
FIG. 4B shows the spectrum of 5 µM myoglobin in 50/50 20 mM ammonium acetate/water, 1% acetic acid with 0.1% ALS-II that had reacted in 10% acetic acid for three days.

Electrospray MS detection of myoglobin in the presence of ALS-II was performed in the same manner as described in Example 3. Myoglobin sample was also prepared with ALS-II that had not been allowed to degrade in acid for an extended period of time. Results (FIG. 4) show that degradation of surfactant is required for detection of myoglobin.

Figure 5B:
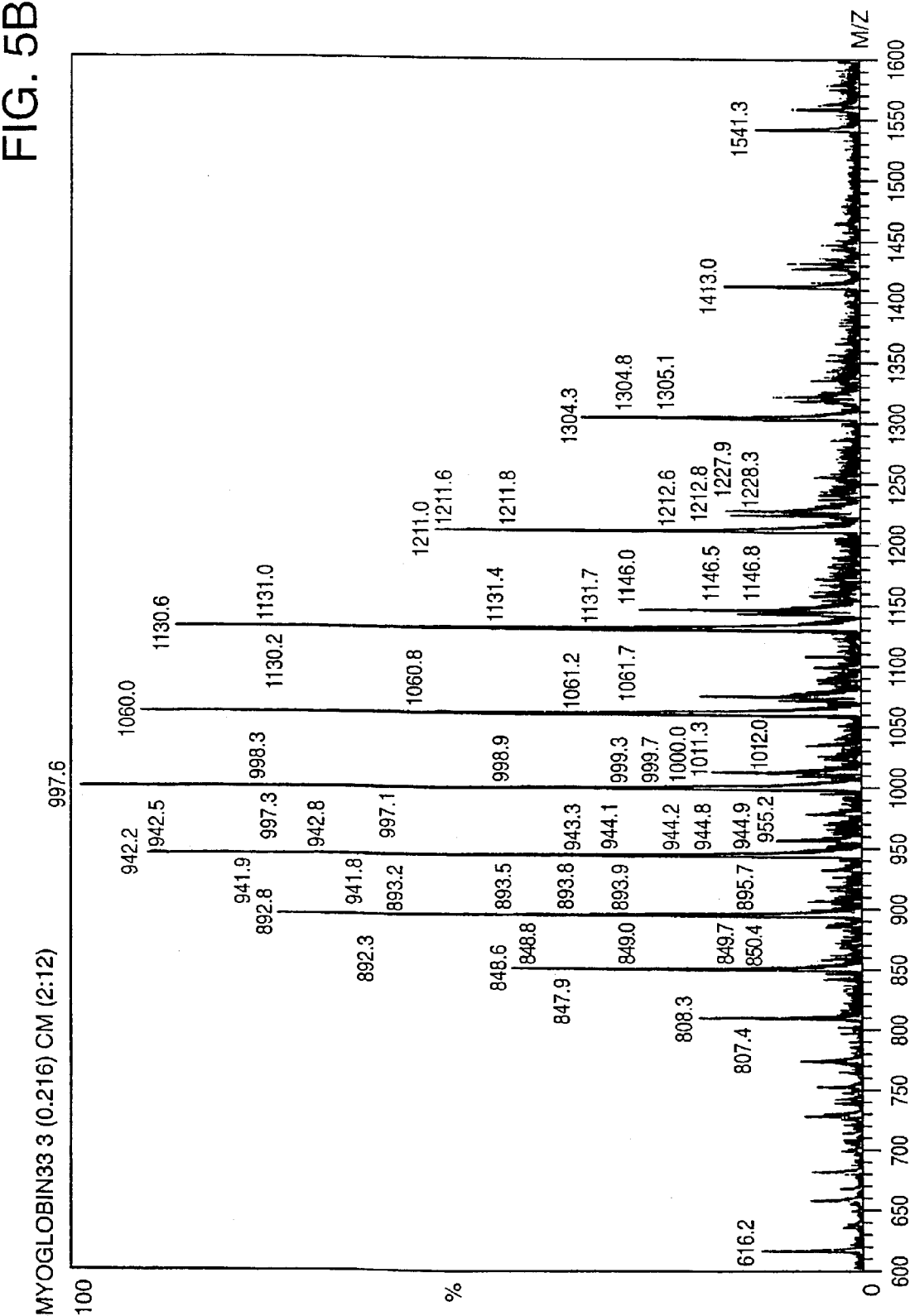
FIG. 5B shows the spectrum of 5 µM myoglobin in 50/50 20 mM ammonium acetate/water, 1% acetic acid and 0.01% ALS-II (w/v).
Figure 5C:
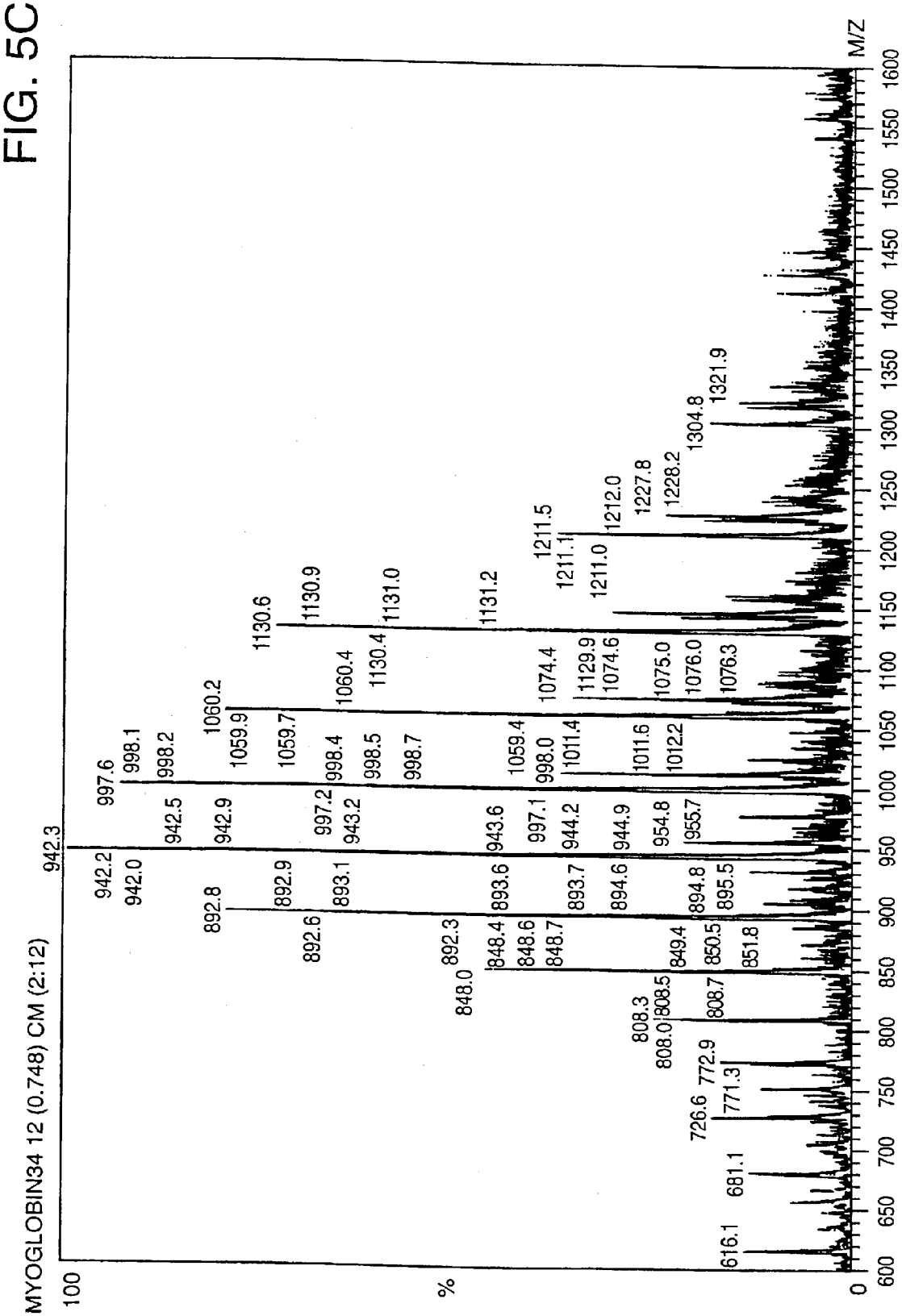
FIG. 5C shows the spectrum of 5 µM myoglobin in 50/50 20 mM ammonium acetate/water, 1% acetic acid and 0.02% ALS-II (w/v).
Figure 6A:
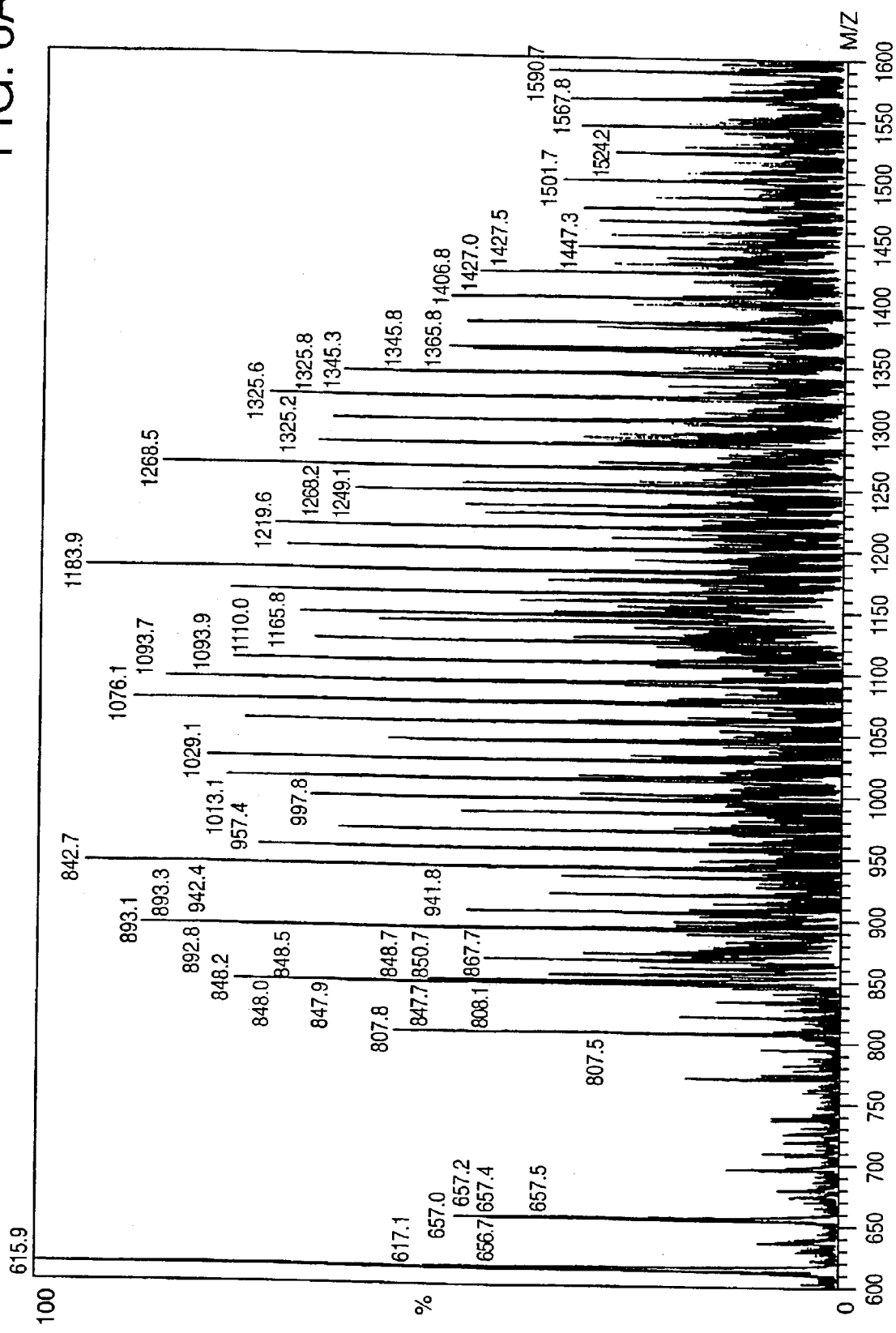
FIG. 6A shows the spectrum of 5 µM myoglobin in 50/50 20 mM ammonium acetate/water, 1% acetic acid and 0.005% SDS (w/v).
Figure 6B:
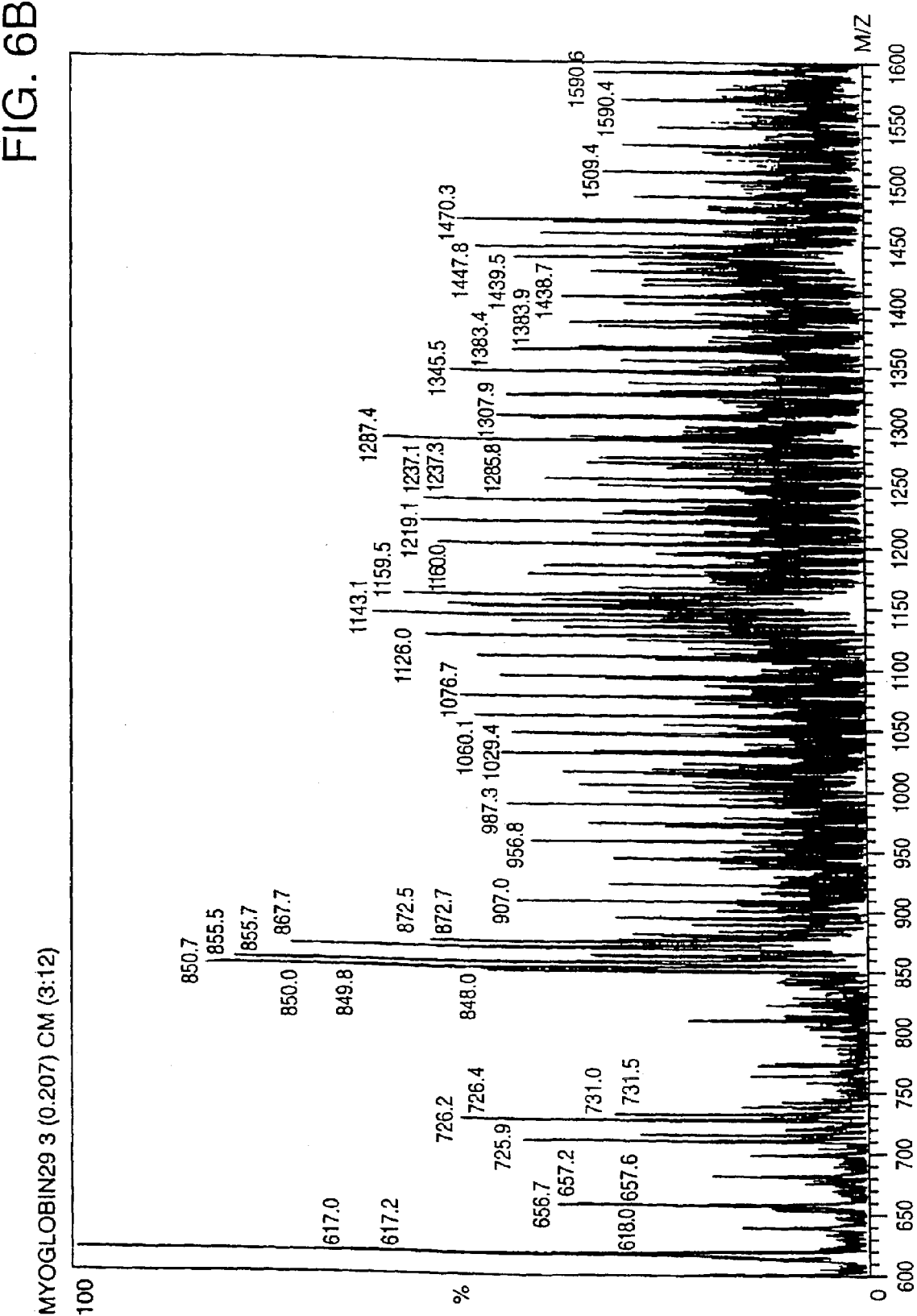
FIG. 6B shows the spectrum of 5 µM myoglobin in 50/50 20 mM ammonium acetate/water, 1% acetic acid and 0.01% SDS (w/v).

The effect of surfactant concentration (at 0.005%, 0.01% and 0.02% (w/v)) on myoglobin detection was determined for SDS and degraded ALS-II. Mass spectra, shown in FIGS. 5 and 6 show that even at 0.005% SDS, detection of myoglobin is extremely difficult due to adduct formation of myoglobin with SDS. On the other hand, detection of myoglobin in the presence of 0.1% ALS-II (degraded) is possible even at the 0.1% level.

Example 8

Preparation of Sodium 4-[(2methyl-2 tridecyl-1,3 dixolan-4-yl)methoxyl]-1-butanesulfonate (9,10) [ALS-III]

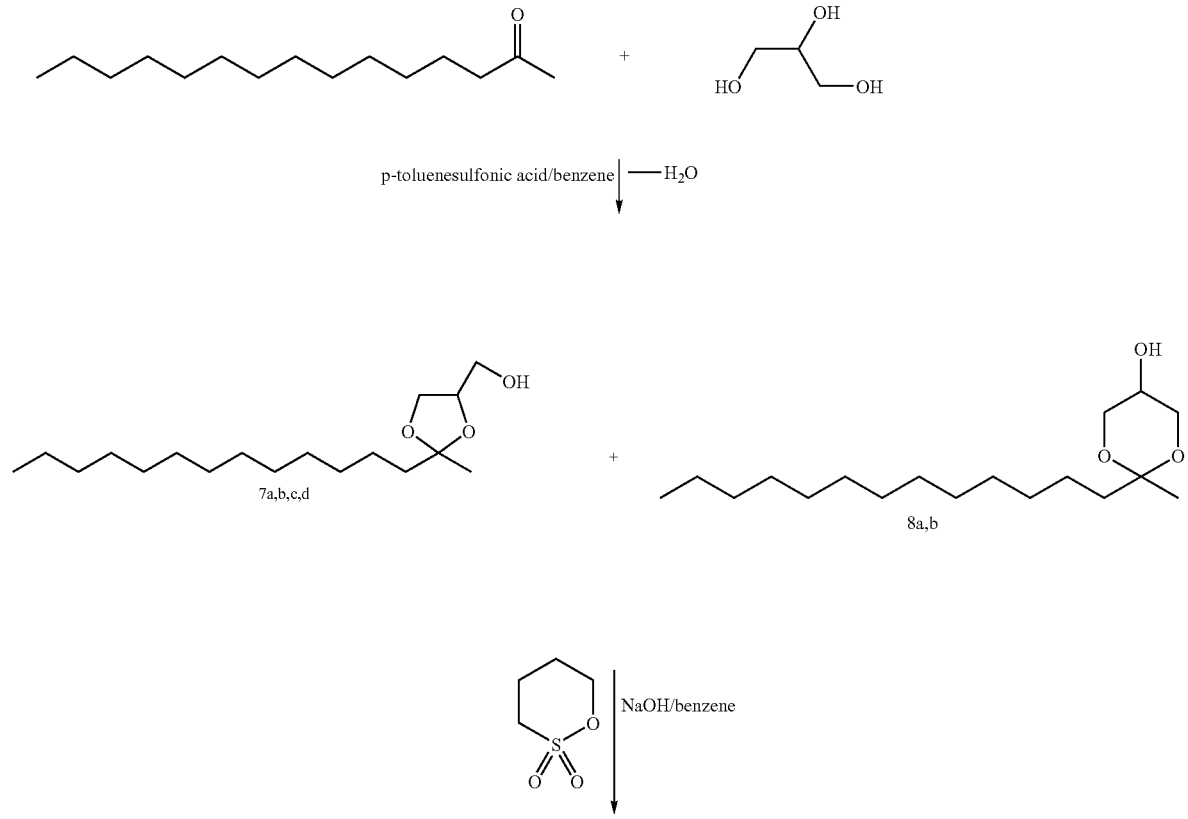

Scheme 3

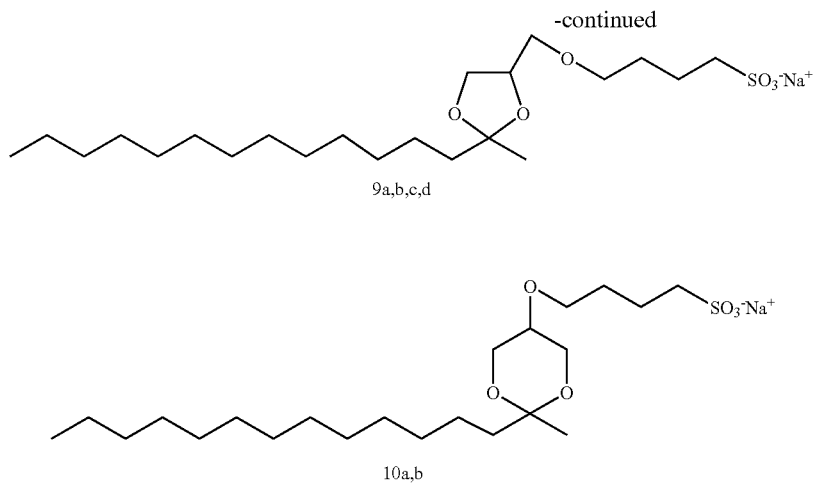

9a,b,c,d 10a,b

This example describes the preparation of certain anionic surfactants of the present invention. Various modifications to the following procedures will be routine to one of ordinary skill in the art, in light of the teachings herein. For example, in the following procedures, toluene may be substituted for benzene. In addition, any solvent that provides a good yield may be used in the recrystalization step.

1. Synthesis of 4 hydroxymethyl-2 methyl-2 tridecyl-1,3 dixolane (7,8):

Firstly, 100 g (0.45 mol) of 2-pentadecanone (Lancaster P/N 9347), 50 g (0.54 mol) of glycerol (Aldrich P/N 32,00-5), 200 mL of benzene, and 1.7 grams of p-toluenesulfonic acid (Aldrich P/N 40,288-5) were placed in a 500 mL round bottom flask fitted with a Dean Stark apparatus. The mixture was heated to reflux with stirring until no further separation of water appeared. The reaction mixture was cooled to room temperature and washed successively with a 100 mL portion of 5% sodium carbonate solution and three 100 mL portions of water. The organic layer was dried over sodium sulfate, filtered and the benzene was removed with a rotary evaporator. The residual oil was fractionated by distillation under reduced pressure to give the desired product. (b.p. 160° C./0.3 mm Hg. The identity of the product was confirmed by $^1$H NMR in $CDCl_3$.

2. Synthesis of ALS-III 100 g (0.32 mol) of 4 hydroxymethyl-2 methyl-2 tridecyl-1,3 dixolane, 14.1 g (0.35 mol) of powdered sodium hydroxide and 200 ml of benzene were placed in a 4 neck 500 mL flask fitted with a condenser, mechanical stirrer and a thermometer. The suspension was stirred at a constant 50° C. while 48 g (0.35 mol) of 1,4 butanesultone (Aldrich P/N B8,550-1) was slowly added over 30 minutes. The suspension was then stirred at 70–75° C. for at least 6 hours. Upon completion, the reaction mixture was poured into 500 mL of boiling ethanol. The resulting mixture is then dried down on a rotary evaporator. The resulting solid is dissolved in boiling ethanol and hot filtered. The solid residue is extracted once with boiling ethanol which is combined with the mother liquor. The solvent is removed in a rotary evaporator. The residue is then recrystallized from ethanol to yield the product. Identity of the product was confirmed by $^1$H NMR in $D_2O$.

Example 9

Mass Spectrometric Detection of Myoglobin Treated with ALS-III

This example uses a surfactant of the present invention in mass spectroscopy.

Figure 7:
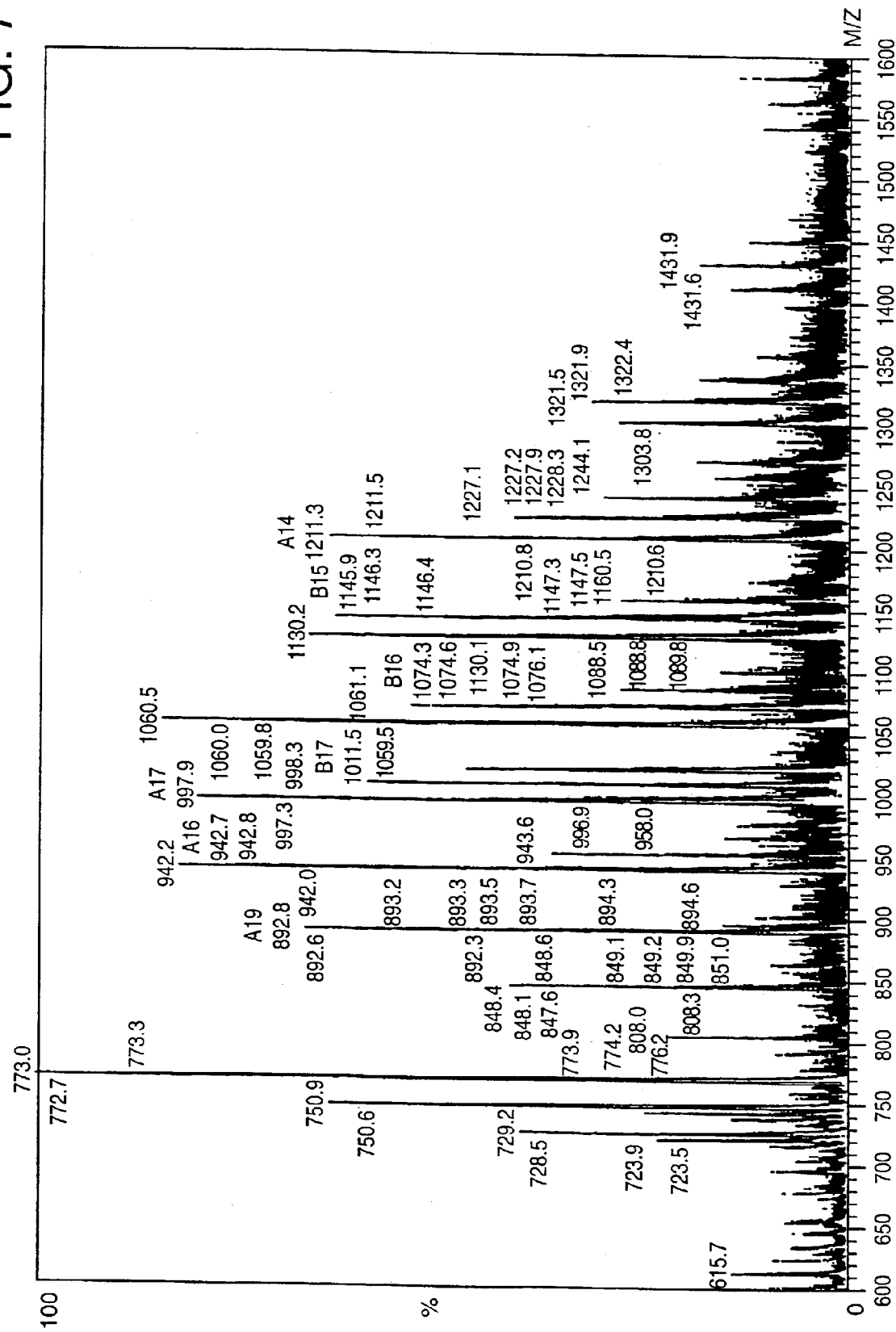
FIG. 7 shows the electrospray mass spectrum of 5 M myoglobin in 50/50 20 mM ammonium acetate/water, 1% acetic acid with 0.1% ALS-III that had reacted in 10% acetic acid for 16 hours.

Electrospray MS detection of myoglobin in the presence of 0.1% ALS-III was performed in the same manner as described in Example 3. Results are shown in FIG. 7.

All patents, published patent applications and other references disclosed herein are hereby expressly incorporated herein in their entireties by reference.

EQUIVALENTS

Those skilled in the art will recognize, or will be able to ascertain using no more than routine experimentation, many equivalents to the specific embodiments of the invention described herein. Such equivalents are intended to be encompassed by the following claims.

The invention claimed is:

1. A method for performing electrophoresis comprising contacting a sample with a surfactant represented by the formula (Formula I):

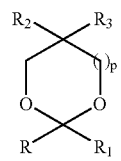

in which p is 0, 1 or 2;

R is alkyl;

$R_1$ and $R_2$ are each, independently, hydrogen or methyl; and $R_3$ is selected from $-OSO_3^-$, $-R_4OSO_3^-$, $-R_4OR_5SO_3^-$, and $-OR_5SO_3^-$, wherein $R_4$ and $R_5$ are each, independently, lower alkyl;

to form a sample/surfactant complex, performing electrophoresis on the sample/surfactant complex.

2. The method of claim 1 comprising the further step of degrading the surfactant after electrophoresis.

3. The method of claim 2 wherein the step of degrading the surfactant after electrophoresis comprises contacting the surfactant with an acidic solution.

4. The method of claim 2 comprising the further step of purifying the sample.

5. The method of claim 1 wherein the surfactant is represented by the following formula:

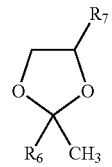

in which
$R_6$ is alkyl;
$R_7$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl.

6. The method of claim 1 wherein the surfactant has the following chemical structure:

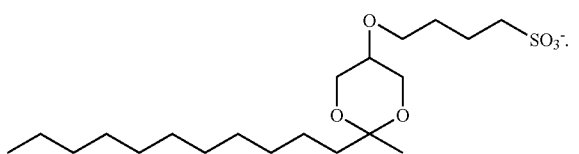

7. The method of claim 1 wherein the surfactant has the following chemical structure:

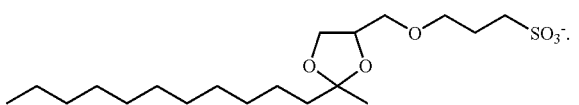

8. A kit for performing electrophoresis comprising:
a surfactant represented by the formula:

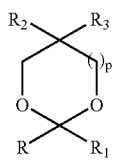

in which
p is 0, 1 or 2;
R is alkyl;
$R_1$ and $R_2$ are each, independently, hydrogen or methyl; and
$R_3$ is selected from $OSO_3^-$, $R_4OSO_3^-$, and $OR_5OSO_3^-$,
wherein $R_4$ and $R_5$ are each, independently, lower alkyl, and
at least one further component selected from the group consisting of a molecular weight standard, a staining reagent and a solution for degrading the surfactant.

9. The kit of claim 8 comprising a solution for degrading the surfactant.

10. The kit of claim 8 wherein the surfactant is represented by the following formula:

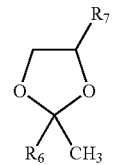

in which
$R_6$ is alkyl;
$R_7$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl.

11. The kit of claim 8 wherein the surfactant has the following chemical structure:

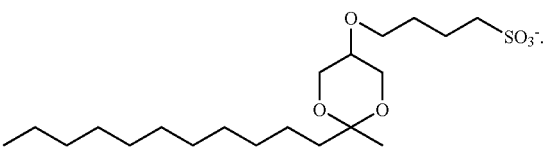

12. The kit of claim 8 wherein the surfactant has the following chemical structure:

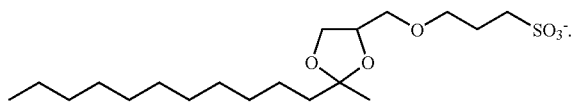

13. A method for analyzing a sample comprising first contacting a sample with a surfactant represented by the formula:

in which
p is 0, 1 or 2;
R is alkyl;
$R_1$ and $R_2$ are each, independently, hydrogen or methyl; and
$R_3$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl; and analyzing the sample.

14. The method of claim 13 wherein the step of analyzing the sample comprises high performance liquid chromatography.

15. The method of claim 13 wherein the step of analyzing the sample comprises mass spectrometric detection.

16. The method of claim 13 wherein the step of analyzing the sample comprises ion-pair liquid chromatography.

17. A surfactant having the following chemical structure:

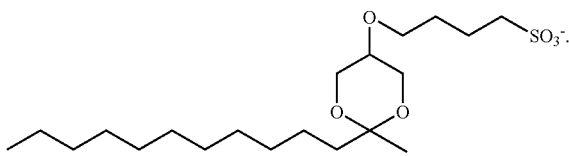

18. A method of synthesizing a surfactant represented by the formula:

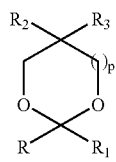

in which p is 0, 1 or 2;

R is alkyl;

$R_1$ and $R_2$ are each, independently, hydrogen or methyl;

$R_3$ is selected from —$OSO_3^-$, —$R_4OSO_3^-$, —$R_4OR_5SO_3^-$, and —$OR_5SO_3^-$, wherein $R_4$ and $R_5$ are each, independently, lower alkyl;

with the provisos that when p is 0 and $R_1$ is methyl, $R_3$ is not —$CH_2O(CH_2)_4SO_3$ or when p is 1 and $R_1$ is hydrogen and $R_2$ is methyl, $R_3$ is not —$CH_2OSO_3$;

the method comprising the step of reacting a compound represented by the formula:

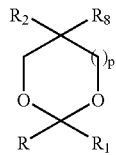

wherein R, $R_1$ and $R_2$ are defined as above and $R_8$ is hydroxyl or —$CH_2OH$, with a compound represented selected from sulfites,

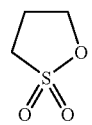

and

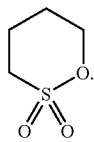

19. A method of solubilizing a substance comprising contacting a substance with a surfactant represented by the formula (Formula I):

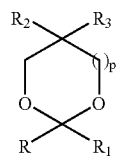

in which p is 0, 1 or 2;

R is alkyl;

$R_1$ and $R_2$ are each, independently, hydrogen or methyl; and $R_3$ is selected from $OSO_3^-$, $R_4OSO_3^-$, and $OR_5OSO_3^-$, wherein $R_4$ and $R_5$ are each, independently, lower alkyl and said substance selected from the group consisting of inclusion bodies, lipophilic proteins, receptors, membrane bound proteins, and biological tissues.

20. A method of regenerating a liquid chromatography column having a sorbent comprising contacting the sorbent with a surfactant represented by the formula (Formula I):

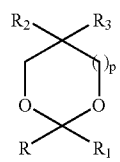

in which p is 0, 1 or 2;

R is alkyl;

$R_1$ and $R_2$ are each, independently, hydrogen or methyl; and $R_3$ is selected from —$OSO_3^-$, —$R_4OSO_3^-$, —$R_4OR_5SO_3^-$, and —$OR_5SO_3^-$, wherein $R_4$ and $R_5$ are each, independently, lower alkyl.

* * * * *